United States Patent
Taillefer et al.

(10) Patent No.: US 9,656,947 B2
(45) Date of Patent: May 23, 2017

(54) PROCESS FOR CREATING CARBON-CARBON BONDS USING CARBONYL COMPOUNDS

(71) Applicants: CENTRE NATIONAL DE LA RECHERCHE SCIENTIFIQUE (C.N.R.S.), Paris (FR); UNIVERSITE MONTPELLIER 2, SCIENCES ET TECHNIQUES, Montpellier (FR); ECOLE NATIONALE SUPERIEURE DE CHIMIE DE MONTPELLIER, Montpellier (FR)

(72) Inventors: Marc Taillefer, Vailhauques (FR); Florian Monnier, Montpellier (FR); Anis Tlili, Montpellier (FR); Grégory Danoun, Montpellier (FR)

(73) Assignees: CENTRE NATIONAL DE LA RECHERCHE SCIENTIFIQUE (C.N.R.S), Paris (FR); UNIVERSITE MONTPELLIER 2, SCIENCES ET TECHNIQUES, Montpellier (FR); ECOLE NATIONALE SUPERIEURE DE CHIMIE DE MONTPELLIER, Montpellier (FR)

( * ) Notice: Subject to any disclaimer, the term of this patent is extended or adjusted under 35 U.S.C. 154(b) by 132 days.

(21) Appl. No.: 14/406,065

(22) PCT Filed: Jun. 6, 2013

(86) PCT No.: PCT/EP2013/061697
§ 371 (c)(1),
(2) Date: Mar. 6, 2015

(87) PCT Pub. No.: WO2013/182640
PCT Pub. Date: Dec. 12, 2013

(65) Prior Publication Data
US 2015/0166464 A1    Jun. 18, 2015

(30) Foreign Application Priority Data
Jun. 6, 2012  (FR) ...................................... 12 55275

(51) Int. Cl.
| | |
|---|---|
| C07C 213/04 | (2006.01) |
| C07C 37/20 | (2006.01) |
| C07B 37/04 | (2006.01) |
| C07C 213/06 | (2006.01) |
| C07C 45/68 | (2006.01) |

(52) U.S. Cl.
CPC ............ *C07C 213/04* (2013.01); *C07B 37/04* (2013.01); *C07C 37/20* (2013.01); *C07C 45/68* (2013.01); *C07C 213/06* (2013.01)

(58) Field of Classification Search
None
See application file for complete search history.

(56) References Cited

FOREIGN PATENT DOCUMENTS

CN        101717408 A    6/2010

OTHER PUBLICATIONS

Chen, Liqun, et al. "Synthesis of multisubstituted furans via copper-catalyzed intramolecular O-vinylation of ketones with vinyl bromides." Tetrahedron Letters51.28 (2010): 3678-3681.
Lashley, Matthew R., and Michael H. Nantz. "Synthesis of lipidic tamoxifen." Tetrahedron Letters 41.18 (2000): 3295-3298.
Stanciuc, Octavian, and Alexandru T. Balaban. "Reaction of pyrylium salts with nucleophiles. 23: Triarylethene derivatives containing an oxyalkyleneamino or oxyalkylene-N-pyridinium side chain." Journal of pharmaceutical sciences 82.9 (1993): 927-933.
Guedira, Nour Eddine, and Rene Beugelmans. "Ambident behavior of ketone enolate anions in SNAr substitutions on fluorobenzonitrile substrates." The Journal of Organic Chemistry 57.21 (1992): 5577-5585.
Skucas, Eduardas, and David WC MacMillan. "Enantioselective α-vinylation of aldehydes via the synergistic combination of copper and amine catalysis." Journal of the American Chemical Society 134.22 (2012): 9090-9093.
Bellina, Fabio, and Renzo Rossi. "Transition Metal-Catalyzed Direct Arylation of Substrates with Activated sp3-Hybridized C—H Bonds and Some of Their Synthetic Equivalents with Aryl Halides and Pseudohalides." Chemical reviews110.2 (2009): 1082-1146.

(Continued)

*Primary Examiner* — Clinton Brooks
(74) *Attorney, Agent, or Firm* — Lathrop & Gage LLP; James H. Velema, Esq.

(57) ABSTRACT

The present invention concerns a process for preparing a compound of formula (I) by reaction between a compound of formula (II) and a compound of formula (III) in the presence of a copper-containing catalyst, a ligand and base. The invention also concerns the implementing of this process for the preparation of building blocks to prepare molecules of interest in particular in the pharmaceutical, agrochemical fields, etc.

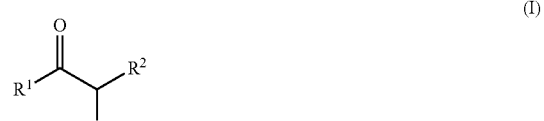

(I)

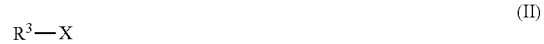

(II)

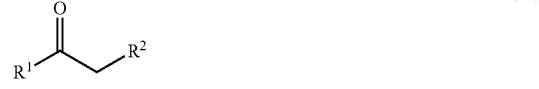

(III)

20 Claims, No Drawings

(56) References Cited

OTHER PUBLICATIONS

Johansson, C. C. C.; Colacot, T. J., Metal-Catalyzed alpha-Arylation of Carbonyl and Related Molecules: Novel Trends in C—C Bond Formation by C—H Bond Functionalization. Angew. Chem.-Int. Edit. 2010, 49 (4), 676-707.
English Translation of Written Opinion of the International Searching Authority for application No. PCT/EP2013/061697, dated Dec. 12, 2013 (7 pages).
International Search Report application No. PCT/EP2013/061697, dated Aug. 23, 2013 2 pages.
Search Report for Application No. FR1255275, dated Feb. 8, 2013 (8 pages).
Office Action corresponding to Chinese Patent Application No. 201380040988.8, issued Sep. 18, 2015.

PROCESS FOR CREATING CARBON-CARBON BONDS USING CARBONYL COMPOUNDS

RELATED APPLICATIONS

This application is a 371 filing of International Application No. PCT/EP2013/061697, filed Jun. 6, 2013, which claims priority to French Patent Application No. 1255275, filed Jun. 6, 2012, the contents of each of which are incorporated herein by reference in their entirety.

The present invention concerns a process for creating carbon-carbon bonds (C—C bonds) from a carbonyl compound, and in particular a process for arylating carbonyl compounds. The invention also concerns the preparation of synthons (building blocks) allowing the preparation of molecules of interest, particularly in the pharmaceutical, cosmetic, agro-chemical fields, etc.

The preparation of numerous families of active molecules, particularly in the pharmaceutical or agro-chemical fields, requires the forming of carbon-carbon bonds (C—C bonds) between a saturated compound and a compound of carbonyl type. The creation of such carbon-carbon bonds can be obtained in particular by arylation of carbonyl compounds, especially alpha arylation of the carbonyl in the carbonyl compound. Usually any molecule resulting from arylation of carbonyl compounds is obtained via palladium catalysis using complex ligands of phosphine type (Bellina et al. Chem. Rev., 2010, 110, 1082-1146 and Johansson et al., Angew. Chem. Int., 2010, 49, 676-707).

However, palladium catalysts and the ligands used in these processes are of high cost and toxic. There is therefore a need to provide a process for creating C—C bonds from a carbonyl compound, and in particular a process to arylate nucleophiles of carbonyl type to solve the disadvantages of prior art processes and which, in particular, is economical and has lesser and even no toxicity.

It is therefore one objective of the invention to provide a process for creating C—C bonds from carbonyl compounds which is economical and is less toxic or even non-toxic.

One particular objective of the invention is to provide a said process which is an arylation process of a carbonyl compound.

A further objective of the present invention is to provide a process for preparing building blocks to produce molecules of interest particularly in the pharmaceutical, agro-chemical fields, etc.

A still further objective of the present invention is to provide a process for preparing molecules of interest particularly in the pharmaceutical, agro-chemical fields etc.

Other objectives will become further apparent on reading the following description of the invention.

This present invention concerns a process for preparing a compound of formula (I) by reaction between a compound of formula (II) and a compound of formula (III) in the presence of a copper-containing catalyst, a ligand and a base.

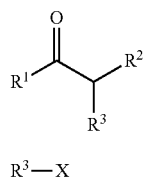
(I)

$R^3$—X (II)

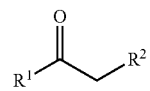
(III)

where:
R$^1$ is:
- a hydrogen atom;
- a straight-chain or branched alkyl group having 1 to 15 carbon atoms;
- a straight-chain or branched alkenyl group having 1 to 15 carbon atoms and comprising at least one double bond;
- a substituted or unsubstituted aryl group having 6 to 10 carbon atoms;
- a substituted or unsubstituted heteroaryl group having 5 to 10 members including at least one heteroatom selected in particular from a nitrogen atom or oxygen atom;

R$^2$ is:
- a straight-chain or branched alkyl group having 1 to 15 carbon atoms;
- a straight-chain or branched alkenyl having 1 to 15 carbon atoms and comprising at least one double bond;
- a substituted or unsubstituted aryl group having 6 to 10 carbon atoms;
- a substituted or unsubstituted heteroaryl group having 5 to 10 members including at least one heteroatom selected in particular from among a nitrogen atom or oxygen atom;

R$^3$ is:
- a substituted or unsubstituted vinyl group;
- a substituted or unsubstituted aryl group having 6 to 10 carbon atoms;
- a substituted or unsubstituted heteroaryl group having 5 to 10 members including at least one heteroatom selected in particular from among a nitrogen atom or oxygen atom;

X is a halogen atom selected from among fluorine, chlorine, bromine or iodine; a tosylate or mesylate Preferably X is a halogen atom selected from among fluorine, chlorine, bromine or iodine.

In one embodiment, the formula (II) compound is a compound of formula (IIa):

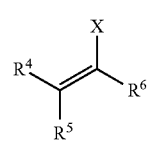
(IIa)

where:
X is such as defined for the compound of formula (II), preferably X is a halogen atom selected from among fluorine, chlorine, bromine or iodine, preferably X is iodine or bromine;

R$^4$, R$^5$ and R$^6$, the same or different are:
- a hydrogen atom;
- a straight-chain or branched alkyl group having 1 to 15 carbon atoms possible comprising one or more unsaturations;

a substituted or non-substituted aryl group having 6 to 10 carbon atoms;
a halogen atom selected from among chlorine, bromine, fluorine and iodine.

In another embodiment, $R^3$ is a heteroaryl having 5 to 10 members including at least one heteroatom selected from among a nitrogen atom or oxygen atom. The heteroaryl can be substituted in particular by one or more substituents selected from among:
  a straight-chain or branched alkyl group of formula —$(O)_n$alkyl having 1 to 15 carbon atoms, preferably 1 to 10 carbon atoms e.g. 1 to 6 carbon atoms, optionally substituted by one or more halogen atoms, preferably fluorine; and n is 0 or 1;
  a straight-chain or branched alkenyl group having 1 to 15 carbon atoms and comprising at least one double bond;
  a halogen atom selected in particular from among chlorine, fluorine, bromine or iodine, preferably fluorine or chlorine;
  CN group; or
  $NH_2$ group.

Preferably the substituents of the heteroaryl are selected from among:
  a straight-chain or branched group of formula —$(O)_n$alkyl having 1 to 15 carbon atoms, preferably 1 to 10 carbon atoms e.g. 1 to 6 carbon atoms, optionally substituted by one or more halogen atoms, preferably fluorine; and n is 0 or 1;
  a straight-chain or branched alkenyl group having 1 to 15 carbon atoms, and comprising at least one double bond;
  a halogen atom selected in particular from among chlorine, fluorine, bromine or iodine, preferably fluorine or chlorine;

In this particular embodiment, preferably X is a halogen atom selected from among fluorine, chlorine, bromine or iodine, preferably X is iodine.

In one preferred embodiment $R^3$ is a substituted or unsubstituted aryl having 6 to 10 carbon atoms. The aryl may be substituted by one or more substituents selected from among:
  a straight-chain or branched group of formula —$(O)_n$alkyl having 1 to 15 carbon atoms, preferably 1 to 10 carbon atoms e.g. 1 to 6 carbon atoms, optionally substituted by one or more halogen atoms, preferably fluorine; and n is 0 or 1;
  a straight-chain or branched alkenyl group having 1 to 15 carbon atoms and comprising at least one double bond;
  a halogen atom selected in particular from among chlorine, fluorine, bromine or iodine, preferably fluorine or chlorine;
  a group of formula CN;
  a group of formula $NH_2$;
  a substituted or unsubstituted aryl group having 6 to 10 carbon atoms;
  a group of formula $(CH_2)_m$-aryl wherein m is an integer ranging from 1 to 10, preferably 1 to 5, and the aryl substituted or unsubstituted has 6 to 10 carbon atoms.

Preferably the aryl can be substituted by one or more substituents selected from among:
  a straight-chain or branched group of formula —$(O)_n$alkyl having 1 to 10 carbon atoms e.g. 1 to 6 carbon atoms, and n is 0 or 1;
  a straight-chain or branched trifluoroalkyl preferably trifluoromethyl group having 1 to 10 carbon atoms;
  a fluorine atom;
  a chlorine atom.

Preferably $R^3$ is a substituted or unsubstituted phenyl.
In this embodiment, preferably X is a halogen atom selected from among fluorine, chlorine, bromine or iodine, preferably X is iodine.

Preferably; in the compounds of formula (I) and (III) according to the invention $R^1$ is selected from among:
  a hydrogen atom;
  a straight-chain or branched alkyl group having 1 to 15 carbon atoms;
  a straight-chain or branched alkenyl group having 1 to 15 carbon atoms, and comprising at least one double bond;
  an aryl group having 6 to 10 carbon atoms unsubstituted or substituted in particular by one or more substituents selected from among:
    a halogen atom selected from among chlorine, bromine, fluorine or iodine; preferably chlorine, bromine or fluorine, more preferably chlorine;
    a hydroxy group;
    a straight-chain or branched group of formula —$(O)_p$alkyl having 1 to 15 carbon atoms, preferably 1 to 10 carbon atoms e.g. 1 to 6 carbon atoms, and p is 0 or 1;
    a straight-chain or branched alkenyl group having 1 to 15 carbon atoms and comprising at least one double bond;
    a straight-chain or branched trifluoroalkyl, preferably trifluoromethyl group having 1 to 10 carbon atoms.

Preferably, in the formula (I) and (III) compounds of the invention $R^1$ is a straight-chain or branched alkyl group having 1 to 15 carbon atoms; or an aryl preferably phenyl group having 6 to 10 carbons atoms unsubstituted or substituted in particular by one or more substituents selected from among:
  a halogen atom selected from among chlorine, bromine, fluorine or iodine, preferably chlorine, bromine or fluorine, preferably chlorine;
  a hydroxy group;
  a straight-chain or branched group of formula —$(O)_p$alkyl having 1 to 15 carbon atoms, preferably 1 to 10 carbon atoms e.g. 1 to 6 carbon atoms, and p is 0 or 1;
  a straight-chain or branched trifluoroalkyl preferably trifluoromethyl group having 1 to 10 carbon atoms.

Preferably, in the formula (I) and (III) compounds of the invention $R^1$ is an aryl group having 6 to 10 carbon atoms, unsubstituted or substituted in particular by one or more substituents selected from among:
  a halogen atom selected from among chlorine, bromine, fluorine or iodine, preferably chlorine, bromine or fluorine, preferably chlorine;
  a hydroxy group;
  a straight-chain or branched group of formula —$(O)_p$alkyl having 1 to 15 carbon atoms, preferably 1 to 10 carbon atoms e.g. 1 to 6 carbon atoms and p is 0 or 1;
  a straight-chain or branched trifluoroalkyl preferably trifluoromethyl group having 1 to 10 carbon atoms.

Preferably in the formula (I) and (III) compounds of the invention $R^1$ is a phenyl, unsubstituted or substituted in particular by one or more substituents from among:
  a halogen atom selected from among chlorine, bromine, fluorine or iodine; preferably chlorine, bromine or fluorine, preferably chlorine;
  a hydroxy group;
  a straight-chain or branched group of formula —$(O)_p$alkyl having 1 to 15 carbon atoms, preferably 1 to 10 carbon atoms e.g. 1 to 6 carbon atoms, and p is 0 or 1;
  a straight-chain or branched trifluoroalkyl preferably trifluoromethyl group having 1 to 5 carbon atoms.

Preferably in the formula (I) and (III) compounds of the invention $R^2$ is selected from among:
- a straight-chain or branched alkyl group having 1 to 15 carbon atoms;
- a straight-chain or branched alkenyl group having 1 to 15 carbon atoms and comprising at least one double bond;
- an aryl group having 6 to 10 carbon atoms unsubstituted or substituted in particular by one or more substituents selected from among:
  - a halogen atom selected from among chlorine, bromine, fluorine or iodine, preferably chlorine, bromine or fluorine;
  - a straight-chain or branched group of formula $-(O)_q$alkyl having 1 to 15 carbon atoms, preferably 1 to 10 carbon atoms e.g. 1 to 6 carbon atoms, and q is 0 or 1;
  - a hydroxy group;
  - a straight-chain or branched alkenyl group having 1 to 15 carbon atoms and comprising at least one double bond;
  - a straight-chain or branched trifluoroalkyl preferably trifluoromethyl group having 1 to 10 carbon atoms.

Preferably in the formula (I) and (III) compounds of the invention $R^2$ is an aryl group having 6 to 10 carbon atoms, unsubstituted or substituted in particular by one or more substituents selected from among:
- a halogen atom selected from among chlorine, bromine, fluorine or iodine; preferably chlorine, bromine or fluorine;
- a straight-chain or branched group of formula $-(O)_q$alkyl having 1 to 15 carbon atoms, preferably 1 to 10 carbon atoms e.g. 1 to 6 carbon atoms, and q is 0 or 1;
- a hydroxy group;
- a straight-chain or branched trifluoroalkyl, preferably trifluoromethyl group having 1 to 10 carbon atoms.

Preferably in the formula (I) and (III) compounds of the invention $R^2$ is a phenyl, unsubstituted or substituted in particular by one or more substituents selected from among:
- a halogen atom selected from among chlorine, bromine, fluorine or iodine; preferably chlorine, bromine or fluorine;
- a hydroxy group;
- a straight-chain or branched group of formula $-(O)_q$alkyl having 1 to 15 carbon atoms, preferably 1 to 10 carbon atoms e.g. 1 to 6 carbon atoms, and q is 0 or 1;
- a straight-chain or branched trifluoroalkyl, preferably trifluoromethyl group having 1 to 5 carbon atoms.

Preferably in the formula (II) compounds X represents iodine.

In the invention the terms below have the following meanings:
- halogen atom: a fluorine, chlorine, bromine or iodine atom;
- alkyl group: a straight-chain or branched, saturated aliphatic group having 1 to 15 carbon atoms. Cited examples are methyl, ethyl, propyl, butyl, ter-butyl . . . .
- alkenyl group: a straight-chain or branched mono- or polyunsaturated aliphatic group having 1 to 15 carbon atoms, e.g. comprising 1 or 2 ethylene unsaturations;
- aryl group: an aromatic cyclic group having 6 to 10 carbon atoms; the said ring optionally being substituted;
- heteroaryl group: an aromatic cyclic group having 5 to 10 members including at least one heteroatom selected in particular from among nitrogen, oxygen and sulfur, preferably nitrogen or oxygen;
- hydroxy group: a group of formula OH.

The catalyst used in the invention is selected in particular from among metallic copper, the oxides of copper(I) or copper(II), the hydroxides of copper(I) or copper(II), the inorganic or organic salts of copper(I) or copper(II) and the complexes of copper(I) or copper(II) with usual ligands, or the mixtures thereof.

Preferred examples of copper-containing catalyst include but are not limited thereto: copper(0), copper halides (e.g. copper(I) iodides, copper(I) bromide, copper(II) bromide, copper(I) chloride, copper(II) chloride), copper oxides or hydroxides (e.g. copper(I) oxide, copper(II) oxide, copper (II) hydroxides), copper nitrates (e.g.: copper(I) nitrate, copper(II) nitrates), copper sulfates or sulfites (e.g. copper(I) sulfate, copper(II) sulfate, copper(I) sulfite), the organic salts of copper in which the counter ions have at least one carbon atom (e.g. copper(II) carbonate, copper(I) acetate, copper(II) acetate, copper(II) trifluoromethylsulfonate, copper(I) methylate, copper(II) methylate, copper(II) acetylacetonate), copper cyanides (CuCN), or the mixtures thereof.

Preferred copper-containing catalysts are copper(0), copper(I) iodide (CuI), copper(II) oxide ($Cu_2O$), copper(II) acetylacetonate (II) [$Cu(acac)_2$], CuI+$Cu(acac)_2$, or the mixtures thereof.

Preferably the copper-containing catalyst is copper iodide CuI.

In one embodiment, the process of the invention is implemented in the presence of a solvent.

The solvent is then selected from the group formed by water, organic solvents and the mixtures thereof, preferably organic solvents and the mixtures thereof and their mixtures with water.

In one embodiment, the organic solvent can be selected from among:
- linear or cyclic carboxamides, preferably N-dimethylacetamide (DMA), N,N-diethylacetamide, dimethylformamide (DMF), diethylformamide or 1-methyl-2-pyrrolidinone (NMP);
- dimethylsulfoxide (DMSO);
- hexamethylphosphotriamide (HMPT);
- tetramethylurea;
- benzene;
- nitro-based compounds, preferably nitromethane, nitroethane, 1-nitropropane, 2-nitropropane or nitrobenzene;
- aliphatic or aromatic nitriles preferably acetonitrile, propionitrile, butanenitrile, isobutanenitrile, pentanenitrile, 2-methylglutaronitrile or adiponitrile;
- tetramethylene sulfone;
- organic carbonates preferably dimethylcarbonate, diisopropylcarbonate or di-n-butylcarbonate;
- alkylated esters preferably ethyl acetate or isopropyl acetate;
- aliphatic or aromatic ethers preferably 1,4-dioxane;
- halogenated or non-halogenated hydrocarbon compounds preferably toluene or chlorobenzene;
- ketones preferably acetone, methylethylketone, methylisobutylketone (MIBK), cyclopentanone, cyclohexanone;
- heterocycles comprising a nitrogen group preferably pyridine, picoline or quinolines;
- alcohols with the exception of ethanol, preferably tert-butanol alone or in a mixture.

The preferred solvents of the invention are dioxane, DMF, DMA, acetonitrile and tert-butanol. Preferably, the solvents are dioxane and tert-butanol.

According to the invention, numerous types of ligand are suitable, in particular bidentate ligands, selected in particular from among:

diketones, in particular of formula (i):

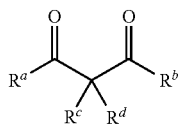 (i)

where:
- $R^a$ and $R^b$, the same or different are a straight-chain or branched $C_1$ to $C_{10}$ alkyl chain, preferably $C_1$ to $C_4$, e.g. t-butyl, methyl, or a $C_6$ to $C_{10}$ aryl radical, phenyl in particular;
- $R^c$ and $R^d$ are a hydrogen atom; or
- $R^a$ or $R^b$ together with their carrier group C(O) and with one of $R^c$ or $R^d$, forms a 6-membered carbocycle; or diamines in particular of formula (ii):

 (ii)

where:
- $R^e$, $R^f$, $R^g$, $R^h$, the same or different, are a hydrogen atom or $C_1$ to $C_{10}$ alkyl group;
- r is an integer between 1 and 10, preferably between 1 and 5; or aromatic polycyclic compounds comprising at least two heteroatoms, in particular nitrogen, in particular tricycles, optionally substituted by one or more $C_1$ to $C_{10}$ alkyl groups, $NO_2$ group, aryl group having 6 to 10 carbon atoms, preferably the polycyclic compound is phenantroline, substituted or unsubstituted.

Advantageously the ligand can be selected from the groups of formula:

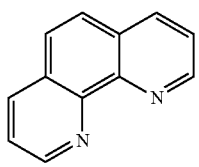 (L1)

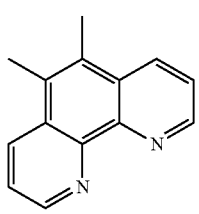 (L2)

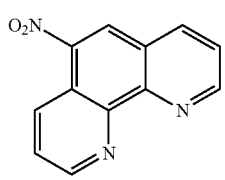 (L3)

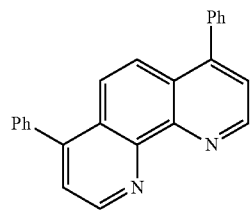 (L4)

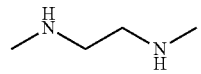 (L5)

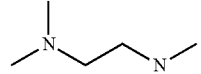 (L6)

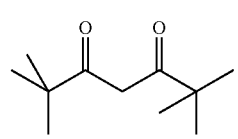 (L7)

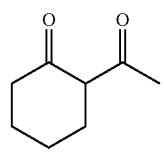 (L8)

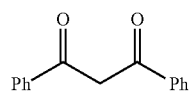 (L9)

where Ph is a phenyl.

Advantageously the ligand is selected from among (L1), (L4) or (L8).

Advantageously:
- the solvent is dioxane and the ligand is selected from among (L1), (L4), (L5), (L6), (L7), (L8) or (L9), preferably (L1), (L4); or
- the solvent is tert-butanol and the ligand is selected from among (L1), (L2), (L3), (L4), (L7) or (L8), preferably (L1), (L2), (L3), (L4) or (L8).

According to the invention, the base can be selected from among alkaline or alkaline-earth alcoholates of formula $(M^1(OR)_s)$ and/or alkaline or alkaline-earth phosphates of formula $(M^1_t(OH)_u(PO_4)_v)$ and/or alkaline or alkaline-earth carbonates of formula $(M^1_w(CO_3)_y)$, or the mixtures thereof.

According to the invention, the base may be an alkaline or alkaline-earth alcoholate of formula $(M^1 (OR)_s)$ where $M^1$ represents Li, Na, K, Rb, Cs, Fr, Be, Mg, Ca, Sr, Ba or Ra, preferably Na; s is 1 or 2, and R is selected from the group formed by the alkyl, benzyl and aryl groups; in particular the base may be potassium terbutylate.

According to the invention, the base may be an alkaline or alkaline-earth phosphate of formula $(M^1_t(OH)_u(PO_4)_v)$ where $M^1$ represents Li, Na, K, Rb, Cs, Fr, Be, Mg, Ca, Sr, Ba or Ra, preferably K; t is an integer ranging from 1 to 10, preferably 1 to 5; u is an integer ranging from 0 to 2 and v is an integer ranging from 1 to 10.

According to the invention, the base may be an alkaline or alkaline-earth carbonate of formula $(M^1_w(CO_3)_y)$ where $M^1$ is selected from the group formed by Li, Na, K, Rb, Cs, Fr, Be, Mg, Ca, Sr, Ba or Ra, preferably Cs or K; w is an integer ranging from 1 to 10, preferably w is 2, and y is an integer ranging from 1 to 10, preferably y is 1; in particular the base may be a caesium carbonate ($Cs_2CO_3$), a potassium carbonate ($K_2CO_3$), or rubidium carbonate ($Rb_2CO_3$).

Advantageously the base can be selected from among $Cs_2CO_3$, $K_2CO_3$ and $Rb_2CO_3$.

Particularly advantageously, the process of the invention can be implemented at lower temperatures than prior art processes using palladium catalysts, thereby allowing energy savings.

For example the process of the invention can be implemented at a temperature ranging from 50 to 200° C., preferably 70 to 150° C.

Preferably the process is implemented at atmospheric pressure, at autogenous pressure of the medium or under slight overpressure.

Preferably in the process of the invention the molar amount of copper-containing catalyst is 0.001 to 100% relative to the number of moles of the formula (II) compound, preferably 0.001 to 50%, more preferably 0.01 to 25%, e.g. from 1 to 20%.

Preferably in the process of the invention the molar ratio of ligand/copper-containing catalyst is 0.5 to 1000, preferably 0.5 to 100, preferably 0.5 to 5, e.g. 1 to 2.

Preferably, in the process of the invention the molar ratio of formula (III) compound/formula (II) compound is 0.5 to 10, preferably 0.5 to 5, in particular 1.5 to 5.

Preferably in the process of the invention the molar quantity of base is 0.2 to 4 equivalents, preferably 0.5 to 2 equivalents, relative to the molar quantity of formula (II) compound.

Usually, the reaction time is between 1 and 36 hours, preferably 12 to 48 hours.

Advantageously the process of the invention allows the preparation of synthons (building blocks) to obtain molecules of interest, in particular in the pharmaceutical, agrochemical fields etc. When thus implemented, the process of the invention has the advantage of being compatible with numerous chemical functions thereby allowing the reducing even avoiding of the need to perform protection/deprotection reactions.

Therefore the invention also concerns a process to prepare building blocks for the obtaining of molecules of interest, comprising the following steps:

1) implementing the process for preparing a compound of formula (I) according to the invention;
2) functionalizing the formula (I) compound using methods known to persons skilled in the art.

Preferably, functionalization may entail for example:

an addition reaction of an organometallic reagent on the carbonyl of the formula (I) compound;
the addition of an alkyl, aryl, heteroaryl group;
an olefination reaction; or
a Shapiro reaction.

In particular, the invention also concerns the preparation of a formula (IV) compound where avec R represents a hydroxy group comprising the implementing of the process to create a carbon-carbon bond according to the invention.

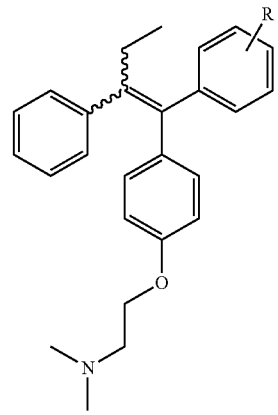

(IV)

Preferably the compounds of formula (IV) are the following compounds:

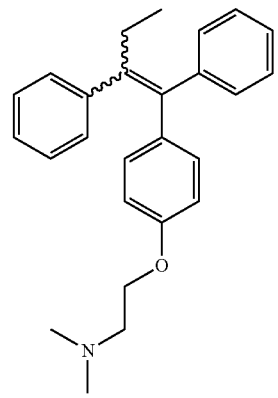

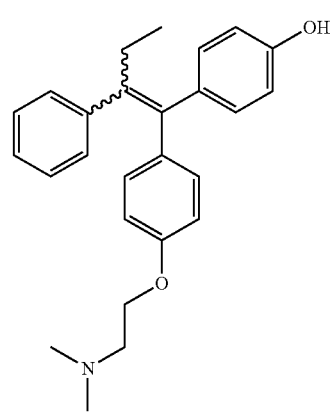

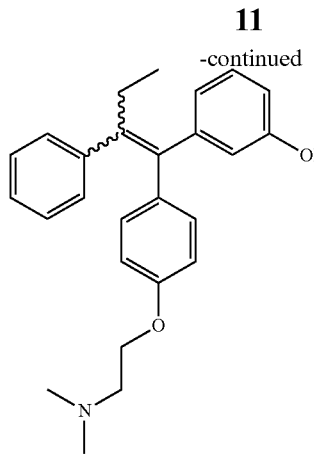
OH, preferably

(V)

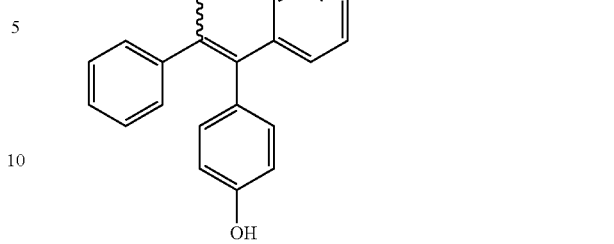

c) reacting the formula (V) compound with a compound of formula Y—(CH$_2$)$_2$N(Me)$_2$ where Y represents a halogen atom, preferably chlorine, to obtain the compound of formula (IV).

In another embodiment, the method to prepare the compound of formula (IV) comprises the following steps:
  a) preparing a formula (Ib) compound by implementing the process to create a C—C bond according to the invention in the presence of a compound of formula Y—C$_6$H$_4$—O—(CH$_2$)$_2$N(Me)$_2$ where Y represents a halogen atom, preferably chlorine:

(Ib)

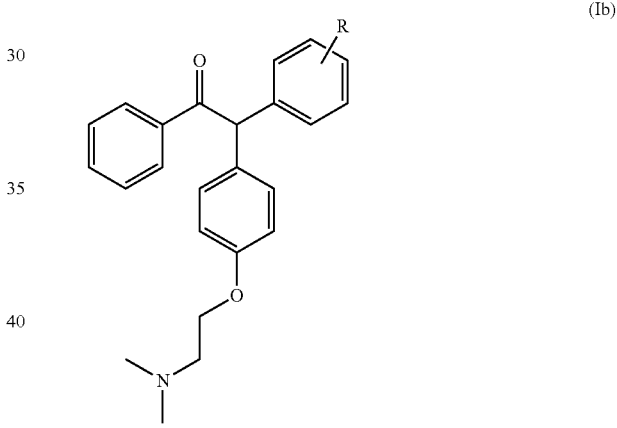

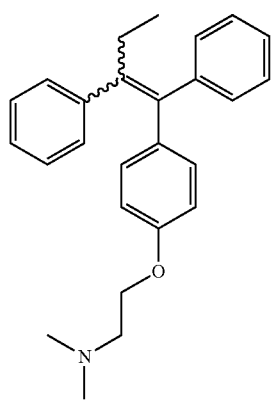

The invention concerns a process for preparing a compound of formula (IV) comprising the preparation of a formula (Ia) compound by carrying out the process to create a C—C bond according to the invention:

(Ia)

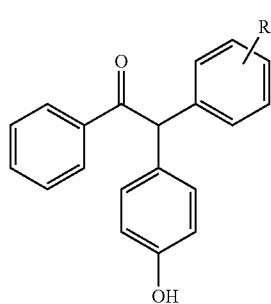

In one embodiment, the process for preparing the formula (IV) compound comprises the following steps:
  a) preparing formula (Ia) compound by implementing the process to create a C—C bond according to the invention;
  b) reacting the formula (Ia) compound with EtMgBr, followed in particular by an elimination reaction using hydrochloric acid in particular, then isomerisation using potassium tert-butanoate in DMSO in particular, to obtain the compound of formula (V):

b) reacting the formula (Ib) compound with EtMgBr to obtain the compound of formula (IV), followed in particular by an elimination reaction with hydrochloric acid in particular, then isomerisation particularly using potassium tert-butanoate in DMSO.

The present invention also concerns compounds of formula (Ia) and compounds of formula (Ib).

The present invention will now be described with the aid of non-limiting examples of embodiments of the process of the invention.

All reactions were performed in 35 ml Schlenk tubes or Radley tubes in a Carousel RR98030 reaction station under nitrogen. The dioxane and tert-butanol were distilled and stored in the presence of a 4 Å molecular sieve under nitrogen. The other solvents were distilled and stored in a nitrogen atmosphere. The reagents used were the following: 95% deoxybenzoin (Alfa Aesar), 99% caesium carbonate (Alfa Aesar), 2-acetylcyclohexanone, phenantroline, 97% anhydrous potassium phosphate (Alfa Aesar), 99.999% CuI (Aldrich). All other solid materials were stored in the presence of P$_4$O$_{10}$ in a vacuum desiccator, at ambient temperature and used without further purification. The formula (II) compounds, in particular aryl iodide were commercially available reagents. Chromatographies were performed with SDS 60 Å on silica gel (35-70 μm). Thin layer chromatographies used 60 F254 silica gels.

All products were characterized by NMR and GC/MS. NMR spectra were performed at 20° C. on a Bruker AC 400 MHz spectrometer or DRX-250 spectrometer operating at 400 MHz for $^1$H and 100 MHz for $^{13}$C respectively. Chemical shifts were recorded in ppm/TMS for $^1$H and $^{13}$C (δ 77.00 for CDCl$_3$ signal). First order peaks are indicated as s (singlet), d (doublet), t (triplet), q (quadruplet). Complex signals are indicated as m (multiplet). HRMS analyses were performed on a JEOL JMS-DX300 spectrometer (3 keV, xenon) in m-nitrobenzylalcohol matrix. The melting points were obtained on Büchi B-540 apparatus.

EXAMPLE 1

Implementation of the Process of the Invention

Procedure (A)

After several standard draining and purging cycles of the tubes using a flow of argon or nitrogen, the reactor is charged with 0.01 mmol (19 mg) of CuI, 1.5 mmol of formula (III) compound, 2 mmol (650 mg) of Cs$_2$CO$_3$, 0.1 mmol of ligand and 1 mmol of formula (II) compound if it is a solid. If the formula (II) compound is a liquid, it is added to the reaction medium using a syringe at ambient temperature followed by the addition of 1 ml of anhydrous or degassed tert-butanol or 1 ml of anhydrous or degassed dioxane. The reactor is closed under positive nitrogen or argon pressure. The reaction mixture is left under agitation and heated to 110° C. for 24 hours. After cooling down to ambient temperature, the reaction mixture is acidified with a 10% aqueous HCl solution and extracted twice with ethyl acetate. The organic phases obtained are combined and washed with brine solution, dried over Na$_2$SO$_4$, filtered and concentrated in vacuo. The product obtained is purified by silica gel chromatography.

1,2-diphenyl-2-p-tolylethanone

EXAMPLE 1.1

Procedure (A) was implemented using:
formula (II) compound: 4-iodotoluene (218 mg, 1.0 mmol),
formula (III) compound: deoxybenzoin,
ligand: bathophenantroline,
solvent: t-BuOH
The yield obtained was 85% (chromatography eluent: petroleum ether/diethylether 95:5)

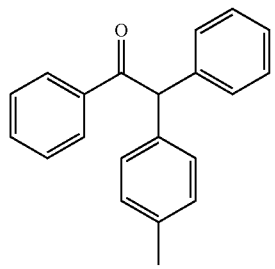 [SMILES: Cc1ccc(C(C(=O)c2ccccc2)c2ccccc2)cc1]

$^1$H NMR (400 MHz, CDCl$_3$) δ ppm 8.06-7.91 (m, 3H); 7.56-7.43 (m, 2H); 7.44-7.34 (m, 2H); 7.34-7.20 (m, 3H); 7.19-7.09 (m, 4H); 6.00 (s, 1H); 2.30 (s, 3H).
$^{13}$C NMR (100 MHz, CDCl$_3$) δ ppm 198.4; 139.4; 136.9; 136.8; 136.1; 133.0; 129.5; 129.1; 129.0; 129.0; 128.7; 128.6; 127.1; 59.1; 21.1.
HRMS calculated for C$_{21}$H$_{19}$O (M+H) 287.1436. Found: 287.1427.

1,2-diphenyl-2-m-tolylethanone

EXAMPLE 1.2

Procedure (A) was implemented using:
formula (II) compound: 3-iodotoluene (130 μL, 1.0 mmol),
formula (III) compound: deoxybenzoin,
ligand: bathophenantroline,
solvent t-BuOH
The yield obtained was 95% (chromatography eluent: petroleum ether/diethylether 95:5).

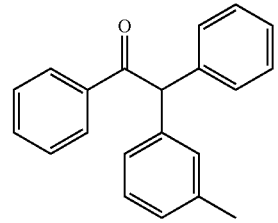 [SMILES: Cc1cccc(C(C(=O)c2ccccc2)c2ccccc2)c1]

$^1$H NMR (400 MHz, CDCl3) δ ppm 7.96-7.87 (m, 3H), 7.63-7.53 (m, 2H), 7.47-7.38 (m, 2H), 7.36-7.28 (m, 1H), 7.27-7.09 (m, 4H), 6.99 (dd, J=13.7, 6.1 Hz, 2H), 5.93 (s, 1H), 2.22 (s, 3H).
$^{13}$C NMR (100 MHz, CDCl$_3$) δ ppm 198.3; 139.2; 138.9; 138.5; 136.9; 135.0; 133.0; 130.0; 129.8; 129.2; 129.1; 129.0; 128.7; 128.6; 128.0; 127.2; 126.2; 59.5; 21.6.
HRMS calculated for C$_{21}$H$_{19}$O (M+H) 287.1436. Found: 287.1441.

2-(3,5-dimethylphenyl)-1,2-diphenylethanone

EXAMPLE 1.3

Procedure (A) was implemented using:
formula (II) compound: 3-iodoxylene (145 μL, 1.0 mmol),
formula (III) compound: deoxybenzoin,
ligand: bathophenantroline,
solvent: t-BuOH
The yield obtained was 95% (chromatography eluent: petroleum ether/diethylether 95:5).

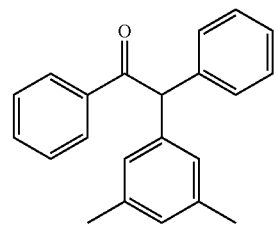 [SMILES: Cc1cc(C)cc(C(C(=O)c2ccccc2)c2ccccc2)c1]

¹H NMR (400 MHz, CDCl₃) δ ppm 7.97-7.85 (m, 3H); 7.48-7.37 (m, 2H); 7.36-7.28 (m, 2H); 7.27-7.11 (m, 3H); 6.89-6.70 (m, 3H); 5.89 (d, J=2.55 Hz, 1H); 2.18 (s, 6H).
¹³C NMR (100 MHz, CDCl₃) δ ppm 198.3; 139.2; 138.7; 138.2; 136.9; 132.9; 129.9; 129.1; 128.9; 128.6; 128.5; 127.0; 126.8; 59.3; 21.3.
HRMS calculated for $C_{22}H_{21}O$ (M+H) 301.1592. Found: 301.1589.

2-(4-methoxyphenyl)-1,2-diphenylethanone

EXAMPLE 1.4

Procedure (A) was implemented using:
formula (II) compound: 4-iodoanisole (234 mg, 1.0 mmol),
formula (III) compound: deoxybenzoin,
ligand: phenantroline,
solvent: t-BuOH
The yield obtained was 74% (chromatography eluent: petroleum ether/toluene 1:1).

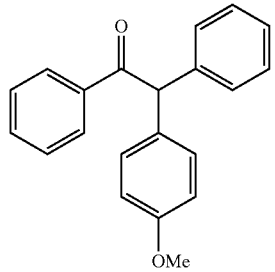 [SMILES: COc1ccc(C(C(=O)c2ccccc2)c2ccccc2)cc1]

¹H NMR (400 MHz, CDCl₃) δ ppm 7.92 (dd, J=8.4, 1.2 Hz, 2H), 7.48-7.39 (m, 1H), 7.37-7.29 (m, 2H), 7.24 (ddd, J=7.1, 4.5, 1.2 Hz, 2H), 7.20-7.15 (m, 3H), 7.14-7.09 (m, 2H), 6.82-6.73 (m, 2H), 5.91 (s, 1H), 3.69 (s, 3H).
¹³C NMR (100 MHz, CDCl₃) δ ppm 198.5; 158.7; 158.3; 139.5; 136.9; 133.0; 131.1; 130.2; 129.1; 129.0; 128.7; 128.6; 127.1; 114.2; 58.7; 55.3.
HRMS calculated for $C_{21}H_{19}O_2$ (M+H) 303.1385. Found: 303.1388.

2-(3-methoxyphenyl)-1,2-diphenylethanone

EXAMPLE 1.5

Procedure (A) was implemented using:
formula (II) compound: 3-iodoanisole (120 µl, 1.0 mmol),
formula (III) compound: deoxybenzoin,
ligand: bathophenantroline,
solvent: t-BuOH
The yield obtained was 83% (chromatography eluent: petroleum ether/toluene 1:1).

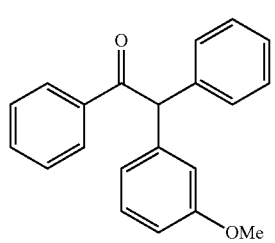 [SMILES: COc1cccc(C(C(=O)c2ccccc2)c2ccccc2)c1]

¹H NMR (400 MHz, CDCl₃) δ ppm 7.95-7.89 (m, 2H), 7.48-7.37 (m, 1H), 7.36-7.28 (m, 2H), 7.27-7.11 (m, 6H), 6.79 (dd, J=7.4, 0.7 Hz, 1H), 6.76-6.74 (m, 1H), 6.71 (ddd, J=8.2, 2.6, 0.7 Hz, 1H), 5.93 (s, 1H), 3.67 (s, 3H).
¹³C NMR (100 MHz, CDCl₃) δ ppm 195.7, 157.4, 138.1, 136.5, 134.5, 130.7, 127.3, 126.8, 126.6, 126.3, 126.3, 124.8, 119.2, 112.7, 110.0, 57.0, 52.8.
HRMS calculated for $C_{21}H_{19}O_2$ (M+H) 303.1385. Found: 303.1375.

2-(2-methoxyphenyl)-1,2-diphenylethanone

EXAMPLE 1.6

Procedure (A) was implemented using:
formula (II) compound: 2-iodoanisole (130 µl, 1.0 mmol),
formula (III) compound: deoxybenzoin,
ligand: phenantroline,
solvent: t-BuOH
The yield obtained was 50% (chromatography eluent: petroleum ether/toluene 1:1).

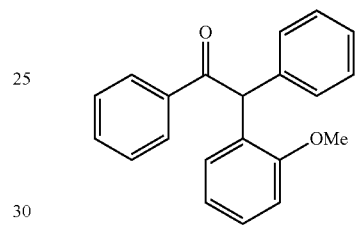

¹H NMR (400 MHz, CDCl₃) δ ppm 8.14-7.77 (m, 2H), 7.44-7.35 (m, 1H), 7.34-7.26 (m, 2H), 7.27-7.21 (m, 4H), 7.21-7.11 (m, 2H), 6.84 (dd, J=7.4, 1.8 Hz, 1H), 6.78 (dd, J=11.5, 4.3 Hz, 2H), 6.26 (s, 1H), 3.67 (s, 3H).
¹³C NMR (100 MHz, CDCl₃) δ ppm 198.9; 156.3; 137.6; 137.1; 132.7; 129.8; 128.8; 128.8; 128.5; 128.4; 127.2; 120.7; 110.4; 55.5; 53.1.
HRMS calculated for $C_{21}H_{19}O_2$ (M+H) 303.1385. Found: 303.1378.

1-phenyl-2,2-dip-tolylethanone

EXAMPLE 1.7

Procedure (A) was implemented using:
formula (II) compound: 4-iodotoluene (218 mg, 1.0 mmol),
formula (III) compound: 4-methylbenzylphenylketone,
ligand: bathophenantroline,
solvent: t-BuOH
The yield obtained was 70% (chromatography eluent: petroleum ether/diethylether 95:5).

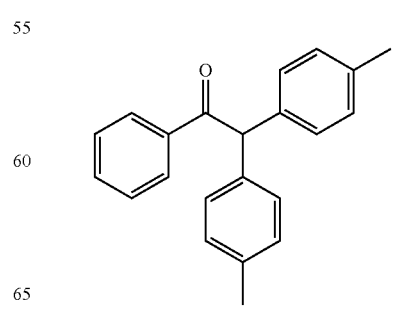

$^1$H NMR (400 MHz, CDCl$_3$) δ ppm 8.11-7.72 (m, 2H); 7.48-7.37 (m, 1H); 7.36-7.28 (m, 2H); 7.13-6.98 (m, 8H); 5.88 (s, 1H); 2.23 (s, 6H).

$^{13}$C NMR (100 MHz, CDCl$_3$) δ ppm 198.5; 137.0; 136.7; 136.3; 132.9; 129.4; 129.0; 128.6; 58.8; 21.1.

HRMS calculated for C$_{22}$H$_{21}$O (M+H) 301.1592. Found: 301.1588.

1-phenyl-2-m-tolyl-2-p-tolylethanone

EXAMPLE 1.8

Procedure (A) was implemented using:
formula (II) compound: 3-iodotoluene (130 μL, 1.0 mmol),
formula (III) compound: 4-methylbenzylphenylketone,
ligand: phenantroline,
solvent: t-BuOH The yield obtained was 54% (chromatography eluent: petroleum ether/diethylether 95:5).

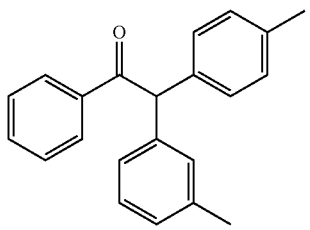 [SMILES: Cc1ccc(C(C(=O)c2ccccc2)c2cccc(C)c2)cc1]

$^1$H NMR (400 MHz, CDCl$_3$) δ ppm 7.98-7.85 (m, 2H); 7.46-7.37 (m, 1H); 7.37-7.27 (m, 2H); 7.18-7.02 (m, 5H); 7.02-6.94 (m, 3H); 5.88 (s, 1H); 2.23 (s, 3H); 2.22 (s, 3H).

$^{13}$C NMR (100 MHz, CDCl$_3$) δ ppm 198.4; 139.1; 138.3; 136.9; 136.7; 136.1; 132.9; 129.7; 129.4; 129.0; 128.9; 128.5; 127.9; 126.1; 59.0; 21.5; 21.0.

HRMS calculated for C$_{22}$H$_{21}$O (M+H) 301.1592. Found: 301.1602.

2-(3,5-dimethylphenyl)-1-phenyl-2-p-tolylethanone

EXAMPLE 1.9

Procedure (A) was implemented using:
formula (II) compound: 4-iodoxylene (145 μL, 1.0 mmol),
formula (III) compound: 4-methylbenzylphenylketone,
ligand: bathophenantroline,
solvent: t-BuOH The yield obtained was 90% (chromatography eluent: petroleum ether/diethylether 95:5).

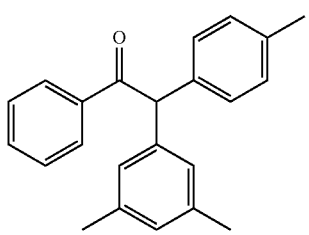 [SMILES: Cc1ccc(C(C(=O)c2ccccc2)c2cc(C)cc(C)c2)cc1]

$^1$H NMR (250 MHz, CDCl$_3$) δ ppm 8.01-7.84 (m, 2H), 7.50-7.38 (m, 1H), 7.39-7.27 (m, 2H), 7.13-7.00 (m, 4H), 6.81 (app s, 3H), 5.86 (s, 1H), 2.24 (s, 3H), 2.19 (s, 6H).

$^{13}$C NMR (100 MHz, CDCl$_3$) δ ppm 198.8, 139.0, 138.4, 137.0, 136.6, 136.2, 132.8, 129.4, 129.1, 128.9, 128.6, 126.9, 58.9, 30.8, 21.1.

HRMS calculated for C$_{23}$H$_{23}$O$_2$ (M+H) 315.1749. Found: 315.1744.

2-(4-methoxyphenyl)-1-phenyl-2-p-tolylethanone

EXAMPLE 1.10

Procedure (A) was implemented using:
formula (II) compound: 4-iodoanisole (234 mg, 1.0 mmol),
formula (III) compound: 4-methylbenzylphenylketone,
ligand: bathophenantroline,
solvent: t-BuOH The yield obtained was 66% (chromatography eluent: petroleum ether/toluene 1:1).

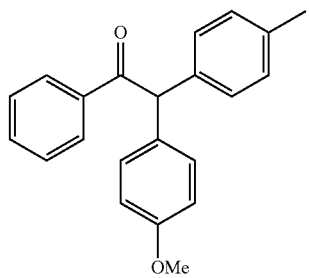 [SMILES: COc1ccc(C(C(=O)c2ccccc2)c2ccc(C)cc2)cc1]

$^1$H NMR (400 MHz, CDCl$_3$) δ ppm 8.08-7.74 (m, 2H), 7.47-7.36 (m, 1H), 7.36-7.25 (m, 2H), 7.18-6.97 (m, 6H), 6.81-6.70 (m, 2H), 5.87 (s, 1H), 3.67 (s, 3H), 2.22 (s, 3H).

$^{13}$C NMR (100 MHz, CDCl$_3$) δ ppm 198.7; 158.6; 136.9; 136.7; 136.5; 133.0; 131.4; 130.2; 129.5; 129.0; 129.0; 128.6; 114.1; 58.3; 55.2; 31.0; 21.1.

HRMS calculated for C$_{22}$H$_{21}$O$_2$ (M+H) 317.1542. Found: 317.1531.

1-(4-chlorophenyl)-2-phenyl-2-p-tolylethanone

EXAMPLE 1.11

Procedure (A) was implemented using:
formula (II) compound: 4-iodotoluene (218 mg, 1.0 mmol),
formula (III) compound: 4-chlorophenylbenzylketone,
ligand: phenantroline,
solvent: dioxane The yield obtained was 95% (chromatography eluent: petroleum ether/diethylether 95:5).

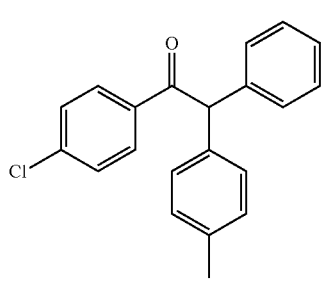 [SMILES: Cc1ccc(C(C(=O)c2ccc(Cl)cc2)c2ccccc2)cc1]

¹H NMR (400 MHz, CDCl₃) δ ppm 7.94-7.73 (m, 2H), 7.31-7.24 (m, 2H), 7.25-7.19 (m, 2H), 7.19-7.12 (m, 3H), 7.09-7.01 (m, 4H), 5.84 (s, 1H), 2.22 (s, 3H).

$^{13}$C NMR (100 MHz, CDCl₃) δ ppm 197.2; 139.4; 139.0; 137.0; 135.7; 135.2; 130.4; 129.6; 129.1; 129.0; 128.9; 128.8; 127.2; 59.3; 21.1.

HRMS calculated for $C_{21}H_{18}OCl$ (M+H) 321.1046. Found: 321.1023.

1-(4-chlorophenyl)-2-phenyl-2-m-tolylethanone

EXAMPLE 1.12

Procedure (A) was implemented using:
formula (II) compound: 3-iodotoluene (130 μL, 1.0 mmol),
formula (III) compound: 4-chlorophenylbenzylketone,
ligand: phenantroline,
solvent: t-BuOH The yield was 96% (chromatography eluent: petroleum ether/diethylether 95:5).

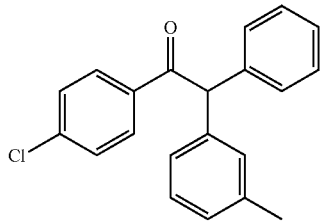 [SMILES: Cc1cccc(C(C(=O)c2ccc(Cl)cc2)c2ccccc2)c1]

¹H NMR (400 MHz, CDCl₃) δ ppm 7.98-7.69 (m, 2H), 7.33-7.27 (m, 2H), 7.27-7.21 (m, 2H), 7.21-7.10 (m, 4H), 7.03-6.93 (m, 3H), 5.85 (s, 1H), 2.23 (s, 3H)

$^{13}$C NMR (100 MHz, CDCl₃) δ ppm, 197.0, 139.5, 138.9, 138.6, 138.5, 135.2, 130.4, 129.7, 129.1, 128.9, 128.7, 128.7, 128.1, 127.2, 126.1, 59.6, 21.5.

HRMS calculated for $C_{21}H_{18}OCl$ (M+H) 321.1046. Found: 321.1046.

1-(4-chlorophenyl)-2-(3,5-dimethylphenyl)-2-phenylethanone

EXAMPLE 1.13

Procedure (A) was implemented using:
formula (II) compound: 3-iodoxylene (145 μL, 1.0 mmol),
formula (III) compound: 4-chlorophenylbenzylketone,
ligand: phenantroline,
solvent: dioxane The yield obtained was 95% (chromatography eluent: petroleum ether/diethylether 95:5).

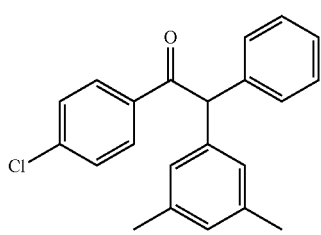 [SMILES: Cc1cc(C)cc(C(C(=O)c2ccc(Cl)cc2)c2ccccc2)c1]

¹H NMR (400 MHz, CDCl₃) δ ppm 8.04-7.67 (m, 3H), 7.47-7.37 (m, 1H), 7.32-7.25 (m, 2H), 7.25-7.20 (m, 1H), 7.20-7.12 (m, 2H), 6.85-6.75 (m, 3H), 5.81 (s, 1H), 2.18 (s, 6H).

$^{13}$C NMR (100 MHz, CDCl₃) δ ppm 197.2, 139.5, 139.0, 138.4, 135.2, 135.1, 131.3, 130.4, 129.2, 129.1, 128.9, 128.7, 126.8, 59.4, 21.5.

HRMS calculated for $C_{22}H_{20}OCl$ (M+H) 335.1203. Found: 335.1189.

1-(4-chlorophenyl)-2-(4-methoxyphenyl)-2-phenylethanone

EXAMPLE 1.14

Procedure (A) was implemented using:
formula (II) compound: 4-iodoanisole (234 mg, 1.0 mmol),
formula (III) compound: 4-chlorophenylbenzylketone,
ligand: phenantroline,
solvent: dioxane The yield obtained was 70% (chromatography eluent: petroleum ether/toluene 1:1).

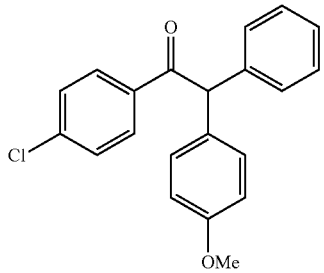 [SMILES: COc1ccc(C(C(=O)c2ccc(Cl)cc2)c2ccccc2)cc1]

$^{x1}$H RMN (400 MHz, CDCl₃) δ ppm 8.00-7.68 (m, 2H); 7.32-7.27 (m, 2H); 7.26-7.21 (m, 2H); 7.20-7.12 (m, 3H); 7.12-7.06 (m, 2H); 6.85-6.70 (m, 2H); 5.83 (s, 1H); 3.69 (s, 3H).

$^{13}$C NMR (100 MHz, CDCl₃) δ ppm 197.2; 158.8; 139.4; 139.1; 135.1; 130.7; 130.3; 130.1; 129.0; 128.9; 128.7; 127.2; 114.2; 58.7; 55.2.

HRMS calculated for $C_{21}H_{18}O_2Cl$ (M+H) 337.0995. Found: 337.0988.

1-(4-chlorophenyl)-2-(3-methoxyphenyl)-2-phenylethanone

EXAMPLE 1.15

Procedure (A) was implemented using:
formula (II) compound: 3-iodoanisole (120 μL, 1.0 mmol),
formula (III) compound: 4-chlorophenylbenzylketone,
ligand: phenantroline,
solvent: dioxane The yield obtained was 75% (chromatography eluent: petroleum ether/toluene 95:5).

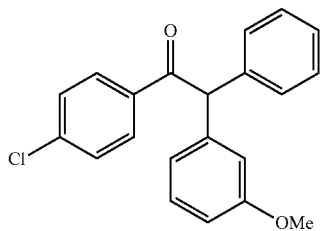 [SMILES: COc1cccc(C(C(=O)c2ccc(Cl)cc2)c2ccccc2)c1]

$^1$H NMR (400 MHz, CDCl$_3$) δ ppm 7.88-7.80 (m, 2H), 7.34-7.26 (m, 2H), 7.26-7.21 (m, 2H), 7.20-7.14 (m, 4H), 6.82-6.74 (m, 1H), 6.74-6.69 (m, 2H), 5.84 (s, 1H), 3.67 (s, 3H).

$^{13}$C NMR (100 MHz, CDCl$_3$) δ ppm 196.8, 160.0, 140.2, 139.5, 138.6, 135.1, 130.4, 129.8, 129.1, 129.0, 128.8, 127.3, 121.6, 115.2, 112.4, 59.5, 55.2.

HRMS calculated for C$_{21}$H$_{18}$O$_2$Cl (M+H) 337.0995. Found: 337.0999.

1-(4-chlorophenyl)-2-(2-methoxyphenyl)-2-phenylethanone

EXAMPLE 1.16

Procedure (A) was implemented using:
formula (II) compound: 2-iodoanisole (130 μL, 1.0 mmol),
formula (III) compound: 4-chlorophenylbenzylketone,
ligand: phenantroline,
solvent: dioxane The yield obtained was 56% (chromatography eluent: petroleum ether/toluene 1:1).

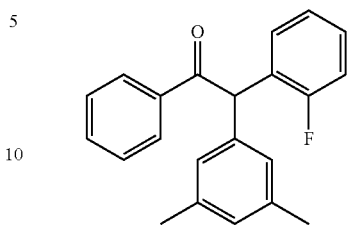

$^1$H NMR (400 MHz, CDCl$_3$) δ ppm 7.89-7.83 (m, 2H), 7.33-7.24 (m, 4H), 7.24-7.19 (m, 3H), 7.18-7.14 (m, 1H), 6.85-6.75 (m, 3H), 6.18 (s, 1H), 3.69 (s, 3H).

$^{13}$C NMR (100 MHz, CDCl$_3$) δ ppm 197.6, 156.2, 139.0, 137.3, 135.4, 131.0, 130.2, 129.7, 128.8, 128.5, 128.4, 127.4, 120.7, 110.5, 55.5, 53.2.

HRMS calculated for C$_{21}$H$_{18}$O$_2$Cl (M+H) 337.0995. Found: 321.0991.

2-(3,5-dimethylphenyl)-2-(2-fluorophenyl)-1-phenylethanone

EXAMPLE 1.17

Procedure (A) was implemented using:
formula (II) compound: 3-iodoxylene (145 μL, 1.0 mmol),
formula (III) compound: 2-fluorobenzylphenylketone,
ligand: bathophenantroline,
solvent: t-BuOH The yield obtained was 96% (chromatography eluent: petroleum ether/diethylether 95:5).

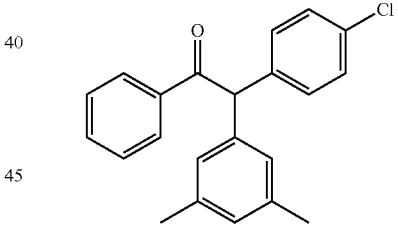

$^1$H NMR (250 MHz, CDCl$_3$) δ ppm 8.04-7.82 (m, 2H), 7.46-7.35 (m, 1H), 7.34-7.27 (m, 2H), 7.18-7.09 (m, 1H), 7.04-6.90 (m, 3H), 6.87-6.80 (m, 3H), 6.16 (s, 1H), 2.19 (s, 6H).

$^{13}$C NMR (100 MHz, CDCl$_3$) δ ppm 197.6, 161.5, 159.0, 138.6, 136.8, 136.5, 133.1, 130.9, 130.8, 129.3, 129.0, 129.0, 129.0, 128.6, 127.2, 127.1, 124.2, 124.1, 115.3, 115.0, 52.0, 21.4.

2-(3,5-dimethylphenyl)-2-(4-chlorophenyl)-1-Phenylethanone

EXAMPLE 1.18

Procedure (A) was implemented using:
formula (II) compound: 3-iodoxylene (145 μL, 1.0 mmol),
formula (III) compound: 4-chlorobenzylphenylketone,
ligand: bathophenantroline,
solvent: t-BuOH The yield obtained was 99% (chromatography eluent: petroleum ether/diethylether 95:5).

$^1$H NMR (250 MHz, CDCl$_3$) δ ppm 8.04-7.78 (m, 2H), 7.52-7.39 (m, 1H), 7.39-7.31 (m, 1H), 7.25-7.18 (m, 2H), 7.15-7.09 (m, 2H), 6.82 (br s, 1H), 6.80 (br s, 2H), 5.85 (s, 1H), 2.20 (s, 6H).

$^{13}$C NMR (100 MHz, CDCl$_3$) δ ppm 198.0, 138.5, 138.3, 137.9, 136.7, 133.2, 133.0, 130.6, 129.2, 129.0, 128.7, 128.7, 126.7, 58.7, 21.3.

Procedure B

After several standard draining and purging cycles of the tubes with a flow or argon or nitrogen, the reactor is charged with 0.01 mmol (19 mg) of CuI, 1.5 mmol of formula (III) compound, 2 mmol (650 mg) of Cs$_2$CO$_3$, 0.1 mmol of 2-acetylcyclohexanone and 1 mmol of formula (II) compound if it is solid. If the formula (II) compound is liquid it is added to the reaction medium using a syringe at ambient temperature with 2-acetylcyclohexanone (0.1 mmol, 13 μL) followed by the addition of 1 ml of anhydrous, degassed tert-butanol. The reactor is closed under positive pressure of nitrogen or argon. The reaction mixture is left under agitation and heated to 70 or 90° C. for 24 hours. After cooling down to ambient temperature, 13 μL of 1,3-dimethoxybenzene (internal standard) then 1 ml of ethyl acetate are added. A sample of the reaction medium is taken and acidified with a 10% aqueous HCl solution, the organic phase is then filtered over celite and the residue washed with ethyl acetate. The filtrate is analysed by proton NMR. The reaction mixture is acidified with a 10% aqueous HCl solution and extracted twice with ethyl acetate. The organic phases obtained are combined and washed in brine solution, dried over Na$_2$SO$_4$, filtered and concentrated in vacuo. The product obtained is purified by silica gel chromatography.

1,2-diphenyl-2-(4-fluorophenyl)ethanone

EXAMPLE 1.19

Procedure (B) was implemented at 70° C. using:
Formula (II) compound: 4-iodofluorobenzene (115 μL, 1.0 mmol)
Formula (III) compound: deoxybenzoin
Product (I) was obtained with a yield of 75% (eluent: petroleum ether/diethylether=95:5).

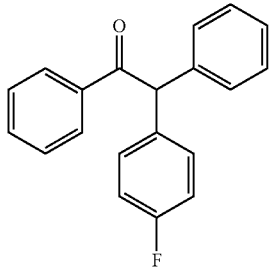 [SMILES: O=C(c1ccccc1)C(c1ccccc1)c1ccc(F)cc1]

$^1$H NMR (400 MHz, CDCl$_3$) δ ppm 7.90 (td, J=8.6, 1.6 Hz, 2H), 7.46-7.35 (m, 1H), 7.36-7.27 (m, 2H), 7.27-7.19 (m, 2H), 7.19-7.10 (m, 5H), 6.98-6.83 (m, 2H), 5.93 (s, 1H)
$^{13}$C NMR (100 MHz, CDCl$_3$) δ ppm 198.0; 163.0; 160.6; 138.8; 136.5; 134.9; 134.8; 133.1; 130.7; 130.6; 128.9; 128.9; 128.8; 128.6; 127.2; 115.6; 115.4; 58.5.
HRMS calculated for C$_{20}$H$_{16}$OF (M+H) 291.1185. Found: 291.1173.

1,2-diphenyl-2-(4-bromophenyl)ethanone

EXAMPLE 1.20

Procedure (B) was implemented at 70° C. using:
Formula (II) compound: 4-iodobromobenzene (283 mg, 1.0 mmol)
Formula (III) compound: deoxybenzoin
Product (I) was obtained with a yield of 60% (eluent: petroleum ether/diethylether 95:5).

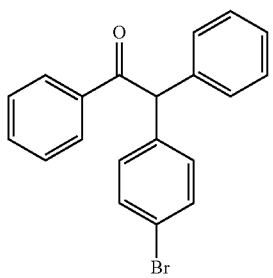 [SMILES: O=C(c1ccccc1)C(c1ccccc1)c1ccc(Br)cc1]

$^1$H NMR (400 MHz, CDCl$_3$) δ ppm 7.90 (td, J=8.6, 1.7 Hz, 2H), 7.49-7.40 (m, 1H), 7.39-7.30 (m, 4H), 7.29-7.21 (m, 2H), 7.21-7.15 (m, 3H), 7.09-7.03 (m, 2H), 5.91 (s, 1H).
$^{13}$C NMR (100 MHz, CDCl$_3$) δ ppm 197.8, 138.5, 138.2, 136.5, 133.3, 131.8, 130.9, 129.0, 129.0, 129.0, 127.4, 121.3, 58.8.

1,2-diphenyl-2-(4-(trifluoromethyl)phenyl)ethanone

EXAMPLE 1.21

Procedure (B) was implemented at 70° C. using:
Formula (II) compound: 4-iodobenzotrifluoride (150 μL, 1.0 mmol)
Formula (III) compound: deoxybenzoin
Product (I) was obtained with a yield of 55% (eluent: petroleum ether/diethylether 95:5).

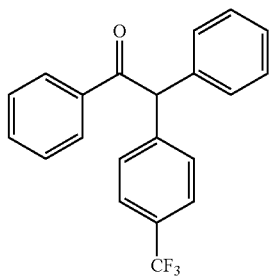 [SMILES: O=C(c1ccccc1)C(c1ccccc1)c1ccc(C(F)(F)F)cc1]

$^1$H NMR (400 MHz, CDCl$_3$) δ ppm 7.94-7.86 (m, 2H), 7.47 (d, J=8.1 Hz, 2H), 7.45-7.39 (m, 1H), 7.35-7.25 (m, 1H), 7.24 (ddd, J=7.1, 4.4, 1.7 Hz, 2H), 7.21-7.16 (m, 3H), 6.00 (s, 1H)
$^{13}$C NMR (100 MHz, CDCl$_3$) δ ppm 197.5, 143.4, 138.2, 136.6, 133.4, 129.6, 129.1, 129.1, 129.0, 128.8, 127.6, 125.6, 59.2.

1,2-diphenyl-2-(3-fluorophenyl)ethanone

EXAMPLE 1.22

Procedure (B) was implemented at 70° C. using:
Formula (II) compound: 3-iodofluorobenzene (120 μL, 1.0 mmol)
Formula (III) compound: deoxybenzoin
Product (I) was obtained with a yield of 48% (eluent: petroleum ether/diethylether 95:5).

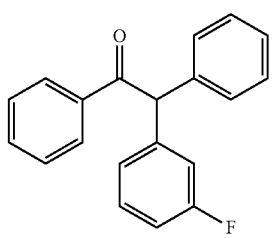 [SMILES: O=C(c1ccccc1)C(c1ccccc1)c1cccc(F)c1]

$^1$H NMR (400 MHz, CDCl$_3$) δ ppm 8.03-7.77 (m, 2H), 7.50-7.30 (m, 3H), 7.29-7.11 (m, 6H), 7.03-6.77 (m, 3H), 5.94 (s, 1H)

$^{13}$C NMR (100 MHz, CDCl$_3$) δ ppm 197.6, 164.9, 160.9, 141.7, 141.6, 138.4, 136.6, 133.3, 130.1, 130.0, 129.1, 129.0, 128.7, 127.5, 124.9, 124.8, 116.5, 116.1, 114.3, 114.0, 59.0.

1,2-diphenyl-2-(3-(trifluoromethyl)phenyl)ethanone

EXAMPLE 1.23

Procedure (B) was implemented at 70° C. using: Formula (II) compound: 3-iodobenzotrifluoride (150 μL, 1.0 mmol)
Formula (III) compound: deoxybenzoin
Product (I) was obtained with a yield of 60% (eluent: petroleum ether/diethylether 95:5).

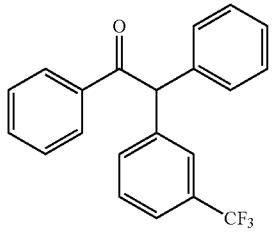 [SMILES: O=C(c1ccccc1)C(c1ccccc1)c1cccc(C(F)(F)F)c1]

$^1$H NMR (400 MHz, CDCl$_3$) δ ppm 7.92 (td, J=8.6, 1.7 Hz, 2H), 7.49-7.41 (m, 3H), 7.40-7.30 (m, 4H), 7.27 (ddd, J=7.1, 4.4, 1.7 Hz, 2H), 7.23-7.18 (m, 3H), 6.01 (s, 1H)
$^{13}$C NMR (100 MHz, CDCl$_3$) δ ppm 197.5, 140.2, 138.2, 136.4, 133.4, 132.7, 129.1, 129.0, 129.0, 128.8, 127.6, 125.9, 124.1, 59.1.

2-(4-fluorophenyl)-1-phenyl-2-p-tolylethanone

EXAMPLE 1.24

Procedure (B) was implemented at 90° C. using::
Formula (II) compound: 4-fluoroiodobenzene (115 μL, 1.0 mmol)
Formula (III) compound: 4-methylbenzylphenylketone
Product (I) was obtained with a yield of 57% (eluent: petroleum ether/diethylether 95:5).

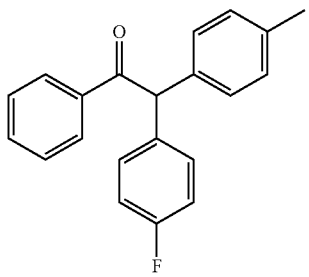 [SMILES: Cc1ccc(C(C(=O)c2ccccc2)c2ccc(F)cc2)cc1]

$^1$H NMR (400 MHz, CDCl$_3$) δ ppm 7.91 (td, J=8.55, 1.69, 1.69 Hz, 2H), 7.48-7.41 (m, 1H), 7.37-7.30 (m, 2H), 7.20-7.10 (m, 3H), 7.10-7.04 (m, 3H), 6.96-6.88 (m, 2H), 5.90 (s, 1H), 2.24 (s, 3H).
$^{13}$C NMR (100 MHz, CDCl$_3$) δ ppm 198.2, 163.1, 160.7, 137.1, 136.7, 135.9, 135.2, 133.2, 130.7, 129.7, 129.0, 128.8, 128.7, 115.6, 115.4, 58.3, 21.1.
HRMS calculated for C$_{21}$H$_{18}$OF (M+H) 305.1342. Found: 305.1335.

2-(3-fluorophenyl)-1-phenyl-2-p-tolylethanone

EXAMPLE 1.25

Procedure (B) was implemented at 90° C. using::
Formula (II) compound: 3-fluoroiodobenzene (115 μL, 1.0 mmol)
Formula (III) compound: 4-methylbenzylphenylketone
Product (I) was obtained with a yield of 54% (eluent: petroleum ether/diethylether 95:5).

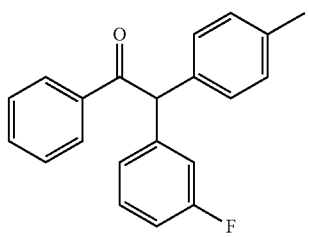 [SMILES: Cc1ccc(C(C(=O)c2ccccc2)c2cccc(F)c2)cc1]

$^1$H NMR (400 MHz, CDCl$_3$) δ ppm 7.90 (td, J=8.6, 1.7 Hz, 2H), 7.48-7.37 (m, 1H), 7.36-7.27 (m, 2H), 7.22-7.13 (m, 1H), 7.12-7.02 (m, 4H), 6.98-6.92 (m, 1H), 6.91-6.80 (m, 2H), 5.90 (s, 1H), 2.22 (s, 3H)
$^{13}$C NMR (100 MHz, CDCl$_3$) δ ppm 197.8, 164.1, 161.7, 141.9, 137.2, 136.7, 135.4, 133.2, 130.0, 129.9, 129.7, 129.0, 128.9, 128.7, 124.8, 124.8, 116.4, 116.2, 114.2, 113.9, 58.6, 21.2.

1-phenyl-2-p-tolyl-2-(3-(trifluoromethyl)phenyl) ethanone

EXAMPLE 1.26

Procedure (B) was implemented at 90° C. using:
Formula (II) compound: 3-iodobenzotrifluoride (150 μL, 1.0 mmol)
Formula (III) compound: 4-methylbenzylphenylketone
Product (I) was obtained with a yield of 40% (eluent: petroleum ether/diethylether 95:5).

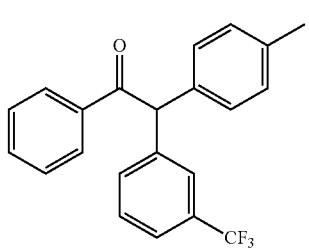 [SMILES: Cc1ccc(C(C(=O)c2ccccc2)c2cccc(C(F)(F)F)c2)cc1]

$^1$H NMR (400 MHz, CDCl$_3$) δ ppm 7.92 (td, J=8.6, 1.6 Hz, 2H), 7.52-7.40 (m, 3H), 7.40-7.30 (m, 4H), 7.14-7.04 (m, 4H), 5.97 (s, 1H), 2.24 (s, 3H).
$^{13}$C NMR (100 MHz, CDCl$_3$) δ ppm 197.6, 140.4, 137.4, 136.5, 135.1, 133.3, 132.7, 129.9, 129.0, 129.0, 128.8, 128.7, 125.9, 124.0, 58.7, 21.1.
HRMS calculated for C$_{22}$H$_{18}$OF$_3$ (M+H) 355.1310. Found: 355.1308.

1-(4-chlorophenyl)-2-(4-fluorophenyl)-2-phenylethanone

EXAMPLE 1.27

Procedure (B) was implemented at 70° C. with:

Formula (II) compound: 4-fluoroiodobenzene (115 μL, 1.0 mmol)

Formula (III) compound: 4-chlorophenylbenzylketone

Product (I) was obtained with a yield of 90% (eluent: petroleum ether/diethylether 95:5).

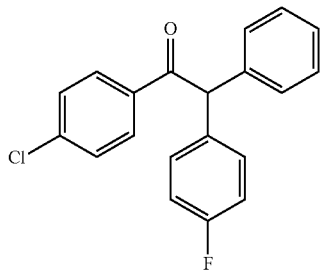 [SMILES: O=C(c1ccc(Cl)cc1)C(c1ccccc1)c1ccc(F)cc1]

$^1$H NMR (400 MHz, CDCl$_3$) δ ppm 7.91-7.74 (m, 2H), 7.31-7.24 (m, 2H), 7.24-7.20 (m, 2H), 7.19-7.07 (m, 5H), 6.96-6.85 (m, 2H), 5.85 (s, 1H)

$^{13}$C NMR (100 MHz, CDCl$_3$) δ ppm 196.9, 163.3, 160.9, 139.7, 138.6, 134.9, 134.6, 130.8, 130.7, 130.4, 129.0, 129.0, 127.5, 115.8, 115.5, 58.7.

HRMS calculated for C$_{20}$H$_{15}$OFCl (M+H) 325.0795. Found: 325.0791.

1,2-bis(4-chlorophenyl)-2-phenylethanone

EXAMPLE 1.28

Procedure (B) was implemented at 70° C. using:

Formula (II) compound: 4-chloroiodobenzene (239 mg, 1.0 mmol)

Formula (III) compound: 4-chlorophenylbenzylketone

Product (I) was obtained with a yield of 75% (eluent: petroleum ether/diethylether 95:5).

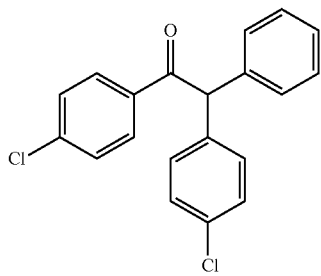 [SMILES: O=C(c1ccc(Cl)cc1)C(c1ccccc1)c1ccc(Cl)cc1]

$^1$H NMR (400 MHz, CDCl$_3$) δ ppm 7.97-7.86 (m, 2H), 7.50-7.41 (m, 1H), 7.38-7.30 (m, 2H), 7.29-7.21 (m, 3H), 7.21-7.16 (m, 3H), 7.15-7.09 (m, 2H), 5.93 (s, 1H).

$^{13}$C NMR (100 MHz, CDCl$_3$) δ ppm 197.8, 138.6, 137.7, 136.5, 133.3, 133.2, 130.6, 129.0, 129.0, 129.0, 128.8, 128.7, 127.4, 58.7.

HRMS calculated for C$_{23}$H$_{14}$OCl$_2$ (M+H) 341.0005. Found: 341.0011.

1-(4-chlorophenyl)-2-phenyl-2-(4-(trifluoromethyl)phenyl)ethanone

EXAMPLE 1.29

Procedure (B) was implemented at 70° C. using:

Formula (II) compound: 4-iodobenzotrifluoride (150 μL, 1.0 mmol)

Formula (III) compound: 4-chlorophenylbenzylketone

Product (I) was obtained with a yield of 35% (eluent: petroleum ether/diethylether 95:5).

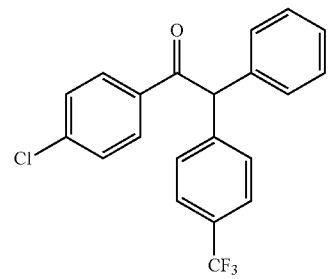 [SMILES: O=C(c1ccc(Cl)cc1)C(c1ccccc1)c1ccc(C(F)(F)F)cc1]

$^1$H NMR (400 MHz, CDCl$_3$) δ ppm 7.86-7.78 (m, 2H), 7.47 (d, J=8.1 Hz, 2H), 7.31-7.21 (m, 6H), 7.21-7.14 (m, 3H), 5.92 (s, 1H).

$^{13}$C NMR (100 MHz, CDCl$_3$) δ ppm 196.3, 142.9, 139.9, 137.8, 134.7, 130.5, 129.6, 129.3, 129.1, 129.0, 127.8, 125.6, 59.3.

HRMS calculated for C$_{21}$H$_{15}$OF$_3$Cl (M+H) 375.0764. Found: 375.0770.

1-(4-chlorophenyl)-2-(3-fluorophenyl)-2-phenylethanone

EXAMPLE 1.30

Procedure (B) was implemented at 70° C. using:

Formula (II) compound: 3-fluoroiodobenzene (120 μL, 1.0 mmol)

Formula (III) compound: 4-chlorophenylbenzylketone

Product (I) was obtained with a yield of 55% (eluent: petroleum ether/diethylether 95:5).

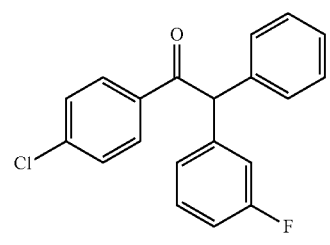 [SMILES: O=C(c1ccc(Cl)cc1)C(c1ccccc1)c1cccc(F)c1]

$^1$H NMR (400 MHz, CDCl$_3$) δ ppm 7.91-7.79 (m, 2H), 7.35-7.24 (m, 4H), 7.23-7.15 (m, 4H), 6.95 (td, J=7.6, 1.4 Hz, 1H), 6.92-6.84 (m, 2H), 5.88 (s, 1H).

$^{13}$C NMR (100 MHz, CDCl$_3$) δ ppm 196.4, 164.2, 161.7, 141.2, 139.8, 138.0, 134.8, 130.4, 130.2, 130.1, 129.2, 129.1, 129.0, 127.6, 124.8, 116.3, 114.3, 59.1.

HRMS calculated for $C_{20}H_{15}OClF$ (M+H) 325.0795. Found: 325.0803.

1-(4-chlorophenyl)-2-phenyl-2-(3-(trifluoromethyl)phenyl)ethanone

EXAMPLE 1.31

Procedure (B) was implemented at 70° C. using:
Formula (II) compound: 3-iodobenzotrifluoride (150 μL, 1.0 mmol)
Formula (III) compound: 4-chlorophenylbenzylketone
Product (I) was obtained with a yield of 20% (eluent: petroleum ether/diethylether 95:5).

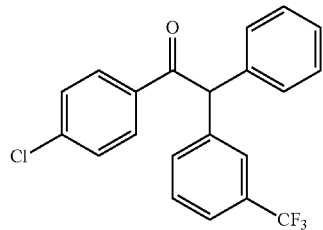 [SMILES: O=C(c1ccc(Cl)cc1)C(c1ccccc1)c1cccc(C(F)(F)F)c1]

$^1$H NMR (400 MHz, CDCl$_3$) δ ppm 7.86-7.79 (m, 2H), 7.47-7.39 (m, 2H), 7.36-7.31 (m, 2H), 7.30-7.26 (m, 2H), 7.26-7.22 (m, 2H), 7.21-7.15 (m, 3H), 5.93 (s, 1H)
$^{13}$C NMR (100 MHz, CDCl$_3$) δ ppm 196.3, 139.9, 139.9, 137.9, 134.7, 132.7, 130.4, 129.3, 129.1, 128.9, 127.8, 125.9, 124.2, 59.2.
HRMS calculated for $C_{21}H_{15}OF_3Cl$ (M+H) 375.0764. Found: 375.0766.

2-(4-fluorophenyl)-2-(4-chlorophenyl)-1-phenylethanone

EXAMPLE 1.32

Procedure (B) was implemented at 70° C. using:
Formula (II) compound: 4-fluoroiodobenzene (115 μL, 1.0 mmol)
Formula (III) compound: 4-chlorophenylbenzylketone
Product (I) was obtained with a yield of 95% (eluent: petroleum ether/diethylether 95:5).

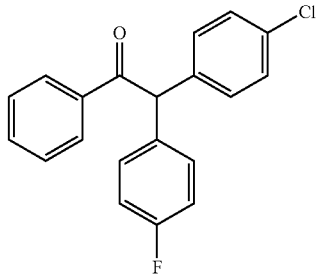 [SMILES: O=C(c1ccccc1)C(c1ccc(F)cc1)c1ccc(Cl)cc1]

$^1$H NMR (400 MHz, CDCl$_3$) δ ppm 7.97-7.83 (m, 2H), 7.54-7.41 (m, 1H), 7.40-7.29 (m, 2H), 7.28-7.05 (m, 6H), 7.01-6.87 (m, 2H), 5.91 (s, 1H).
$^{13}$C NMR (100 MHz, CDCl$_3$) δ ppm 197.7, 163.3, 160.8, 137.4, 136.3, 134.4, 133.4, 133.4, 130.7, 130.6, 130.4, 129.0, 129.0, 128.8, 115.9, 115.7, 57.7.

Procedure C

After several standard draining and purging cycles of the tubes with a flow of argon or nitrogen, the reactor is charged with 0.01 mmol (19 mg) of CuI, 1.5 mmol of formula (III) compound, 2 mmol (650 mg) of Cs$_2$CO$_3$, 0.1 mmol of bathophenanthroline and 1 mmol of formula (II) compound (II) if it is a solid. If the formula (II) compound is a liquid, it is added to the reaction medium using a syringe under a flow of nitrogen at ambient temperature followed by the addition of 1 ml of anhydrous, degassed de tert-butanol. The reactor is closed under positive pressure of nitrogen or argon. The reaction mixture is left under agitation and heated to 110° C. for 24 hours. After cooling down to ambient temperature, 13 μL of 1,3-dimethoxybenzene (internal standard) then 1 ml of ethyl acetate are added. A sample of the reaction medium is taken and acidified with 10% aqueous HCl solution, the organic phase is then filtered through celite and the residue washed in ethyl acetate. The organic phases obtained are combined and washed with brine solution, dried over Na$_2$SO$_4$, filtered and concentrated in vacuo. The product obtained is purified by silica gel chromatography and analysed by NMR.

The results obtained are summarised in the Table below:

| Examples | Formula (I) compound | Formula (II) compound | Formula (III) compound | Yield (%) |
|---|---|---|---|---|
| Example 1.33 | ![structure] | I-C6H4-CH3 | ![structure] | 10 |

-continued

| Examples | Formula (I) compound | Formula (II) compound | Formula (III) compound | Yield (%) |
|---|---|---|---|---|
| Example 1.34 | Br-C6H4-CH(4-MeC6H4)-CO-CH3 | 4-iodotoluene | Br-C6H4-CH2-CO-CH3 | 17 |
| Example 1.35 | Br-C6H4-CH(Ph)-CO-CH3 | iodobenzene | Br-C6H4-CH2-CO-CH3 | 15 |
| Example 1.36 | Ph-CH(4-MeOC6H4)-CO-CH3 | 4-iodoanisole | Ph-CH2-CO-CH3 | 11 |
| Example 1.37 | Ph-CH(Ph)-CO-CH3 | iodobenzene | Ph-CH2-CO-CH3 | 11 |

EXAMPLE 2

Influence of the Catalyst, of the Solvent and of the Base

The process of the invention was carried out in accordance with procedure A using different solvents, different bases (2 mmol) and different catalysts (10 mole % relative to the formula (III) compound), using 4-methyliodobenzene (1 mmol) as formula (II) compound and deoxybenzoin (1.5 mmol) as formula (III) compound, and compound L1 (0.1 mmol) as ligand. The yield was determined by NMR using 1,3 dimethoxybenzene as internal standard.

The results are given in Table (1):

TABLE 1

| Solvent | Catalyst | Base | Yield [%] |
|---|---|---|---|
| DMF or $CH_3CN$ | CuI | $Cs_2CO_3$ | 10 |
| DMA | CuI | $Cs_2CO_3$ | 17 |
| t-BuOH | CuI | $Cs_2CO_3$ | 52 |
| dioxane | CuI | $Cs_2CO_3$ | 70 |
| dioxane | CuI | $Rb_2CO_3$ ou $K_2CO_3$ | 18-21 |
| dioxane | $Cu(acac)_2$ | $Cs_2CO_3$ | 30 |
| dioxane | $Cu(OTf)_2$ ou $Cu_2O$ | $Cs_2CO_3$ | 43-45 |
| dioxane | CuCl, $Cu(Oac)_2$, $CuBr_2$, or CuCN | $Cs_2CO_3$ | 48-51 |

These results show that the process of the invention can advantageously be implemented using various catalysts, bases and solvents.

EXAMPLE 3

Influence of the Ligand and Solvent

The process of the invention was carried out following procedure A at 110° C. using different solvents and different ligands (10 mole % relative to the formula (III) compound), using 4-methyliodobenzene (1 mmol) as formula (II) compound, deoxybenzoin (1.5 mmol) as formula (III) compound, $Cs_2CO_3$ (2 mmol) as base and CuI as catalyst (10 mole % relative to the formula (III) compound). The yield was determined by NMR using 1,3 dimethoxybenzene as internal standard.

The results are given in Table (2):

TABLE 2

| | Yield [%] | |
|---|---|---|
| Ligand | Solvent dioxane | Solvent t-BuOH |
| — | 8 | 6 |
| L1 | 70 | 52 |
| L2 | 27 | 46 |
| L3 | 3 | 47 |
| L4 | 68 | 84 |
| L5 | 29 | 5 |
| L6 | 23 | 8 |
| L7 | 20 | 17 |
| L8 | 24 | 58 |
| L9 | 11 | 8 |

These results show that the process of the invention can advantageously be implemented using various ligands and solvents and evidences some preferred combinations.

EXAMPLE 4

Synthesis of Tamoxifen (Compound of Formula (IV))

After several purging cycles with argon a Schlenk tube fitted with a magnetic stir bar is charged with CuI (0.1 mmol, 19 mg), deoxybenzoin (294 mg, 1.5 mmol), $Cs_2CO_3$ (4 mmol, 1.3 g) and 4-iodophenol (220 mg, 1 mmol). The tube is purged with argon after which 2-acetylcyclohexanone (0.1 mmol, 13 μL) is added using a syringe in a nitrogen atmosphere at ambient temperature, followed by the addition of 1 mL of anhydrous t-BuOH (1.0 mL). The tube is sealed under positive argon pressure and the reaction mixture is left under agitation and heated to 70° C. for 24 hours. After cooling down to ambient temperature the reaction mixture is acidified with aqueous HCl (37%) for 6 hours. The reaction mixture is then extracted twice with ethyl acetate. The organic phases are collected and washed with brine solution, dried over $Na_2SO_4$, filtered and concentrated in vacuo. The product obtained is purified by silica gel chromatography (eluent: petroleum ether/ethyl acetate 5:5) to give product A with a yield of 82%.

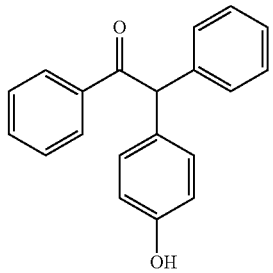 [SMILES: O=C(c1ccccc1)C(c1ccccc1)c1ccc(O)cc1]

$^1$H NMR (400 MHz, $CDCl_3$) δ ppm 8.01-7.84 (m, 2H), 7.51-7.40 (m, 1H), 7.38-7.30 (m, 2H), 7.29-7.21 (m, 2H), 7.20-7.13 (m, 3H), 7.12-7.02 (m, 2H), 6.76-6.66 (m, 2H), 5.90 (s, 1H).

$^{13}$C NMR (100 MHz, $CDCl_3$) δ ppm 198.7, 154.8, 139.4, 136.8, 133.1, 131.3, 130.4, 129.1, 129.0, 128.7, 128.6, 127.1, 115.7, Product A: 58.6.

To a solution of product A (100 mg, 0.347 mmol) in THF (3 mL), EtMgBr (350 μL, 1.04 mmol) was added at −78° C. and the mixture left under agitation for 5 hours at ambient temperature. The resulting reaction mixture was hydrolysed with water, extracted three times with ethyl acetate. The organic phases obtained were combined, washed with brine solution, dried over $Na_2SO_4$, filtered and concentrated in vacuo. The product thus obtained was diluted with methanol and aqueous HCl (37%) was added. The resulting reaction mixture was left under agitation and refluxed for 15 hours. The solvent and HCl were removed by evaporation in vacuo. The crude was re-dissolved in ethyl acetate and water was added. The mixture was then extracted three times with ethyl acetate, the organic phases were collected, washed in brine solution, dried over $Na_2SO_4$, filtered and concentrated in vacuo. The product obtained was diluted in DMSO (1 mL) and t-BuOK (155.7 mg, 1.39 mmol) was added. The resulting reaction mixture was heated to 50° C. for 2 hours. The reaction mixture was then hydrolysed with saturated aqueous $NH_4Cl$ solution at 0° C., extracted with ethyl acetate and the organic phases were collected, washed in brine solution, dried over $Na_2SO_4$, filtered and concentrated in vacuo. Finally, the crude obtained was diluted in DMF (0.5 mL) and added to NaH solution (41.6 mg, 1.04 mmol) in DMF (0.5 mL) at 0° C. After 30 minutes a 0° C., the hydrochloride of 2-Chloro-N,N-dimethylethylamine (100 mg, 0.69 mmol) was added portion-wise. After 3 hours at 50° C., the mixture was hydrolysed at 0° C. with saturated aqueous $NH_4Cl$ solution. The mixture was then extracted with ethyl acetate, the organic phases collected, washed in brine solution, dried over $Na_2SO_4$, filtered and concentrated in vacuo.

The compound of formula (IV) obtained was purified by chromatography (eluent $CHCl_3$/MeOH/$Et_3N$, 95:5:0.1) to give a 1:1 mixture of conformation compounds Z and E with a yield of 70%.

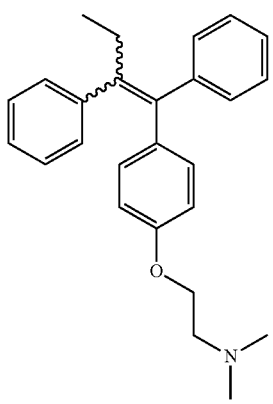

$^1$H NMR (250 MHz, CDCl$_3$) δ ppm 7.36-6.73 (m, 24H), 6.69 (d, J=8.7 Hz, 2H), 6.48 (d, J=8.7 Hz, 2H), 4.01 (t, J=5.8 Hz, 2H), 3.85 (t, J=5.8 Hz, 2H), 2.67 (t, J=5.8 Hz, 2H), 2.57 (t, J=5.8 Hz, 2H), 2.43 (q, J=7.3 Hz, 2H), 2.38 (q, J=7.3 Hz, 2H), 2.28 (s, 6H), 2.21 (s, 6H), 0.87 (t, J=7.3 Hz, 3H), 0.85 (t, J=7.3 Hz, 3H).

$^{13}$C NMR (100 MHz, CDCl$_3$) δ ppm 157.6, 156.7, 144.3, 143.8, 143.3, 143.0, 142.4, 141.9, 141.6, 141.3, 138.4, 138.2, 136.1, 135.5, 134.7, 131.8, 130.8, 130.5, 130.4, 129.7, 129.5, 129.5, 128.8, 128.1, 127.8, 127.8, 127.3, 126.5, 126.0, 125.6, 114.1, 114.1, 113.4, 65.9, 65.6, 58.4, 58.3, 45.9, 45.9, 29.0, 13.6.

The invention claimed is:

1. A process for preparing a compound of formula (I) by reaction between a compound of formula (II) and a compound of formula (III) in the presence of a copper-containing catalyst, a ligand and a base

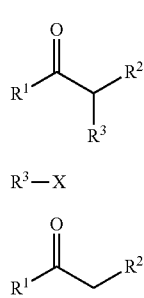

where:
R$^1$ is:
  a hydrogen atom,
  a straight-chain or branched alkyl group having 1 to 15 carbon atoms,
  a straight-chain or branched alkenyl group having 1 to 15 carbon atoms and comprising at least one double bond,
  a substituted or unsubstituted aryl group having 6 to 10 carbon atoms, or
  a substituted or unsubstituted heteroaryl group having 5 to 10 members including at least one heteroatom selected in particular from among a nitrogen atom or oxygen atom;
R$^2$ is:
  a straight-chain or branched alkyl group having 1 to 15 carbon atoms,
  a straight-chain or branched alkenyl group having 1 to 15 carbon atoms and comprising at least one double bond,
  a substituted or unsubstituted aryl group having 6 to 10 carbon atoms, or
  a substituted or unsubstituted heteroaryl group having 5 to 10 members including at least one heteroatom selected in particular from among a nitrogen atom or oxygen atom;
R$^3$ is:
  a substituted or unsubstituted vinyl group,
  a substituted or unsubstituted aryl group having 6 to 10 carbon atoms, or
  a substituted or unsubstituted heteroaryl group having 5 to 10 members including at least one heteroatom selected in particular from among a nitrogen atom or oxygen atom;
X is a halogen atom selected from among fluorine, chlorine, bromine and iodine, a tosylate group, or mesylate group; and
the ligand is selected from among:
  diketones,
  diamines, and
  aromatic polycyclic compounds having at least two heteroatoms, unsubstituted or substituted by one or more C1 to C10 alkyl groups, NO$_2$ group, aryl group having 6 to 10 carbon atoms.

2. The process according to claim 1 wherein R$^3$ represents an aryl having 6 to 10 carbon atoms, unsubstituted or substituted by one or more substituents selected from among:
  a straight-chain or branched group of formula —(O)$_n$alkyl having 1 to 15 carbon atoms, optionally substituted by one or more halogen atoms, and n is 0 or 1;
  a straight-chain or branched alkenyl group having 1 to 15 carbon atoms and comprising at least one double bond;
  a halogen atom selected from among chlorine, fluorine, bromine or iodine;
  a group of formula CN;
  a group of formula NH$_2$;
  a substituted or unsubstituted aryl group having 6 to 10 carbon atoms;
  a group of formula (CH$_2$)$_m$-aryl wherein m is an integer ranging from 1 to 10, and the aryl group, substituted or unsubstituted, comprises 6 to 10 carbon atoms.

3. The process according to claim 1 wherein R$^3$ represents a phenyl substituted by one or more substituents selected from among:
  a straight-chain or branched group of formula —(O)$_n$alkyl having 1 to 10 carbon atoms, and n is 0 or 1;
  a straight-chain or branched trifluoroalkyl group having 1 to 10 carbon atoms;
  a fluorine atom; and
  a chlorine atom.

4. The process according to claim 1 wherein the formula (II) compound is a compound of formula (IIa)

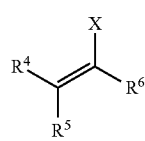

where:
X is such as defined for the formula (II) compound;
$R^4$, $R^5$ and $R^6$, the same or different, represent:
a hydrogen atom;
a straight-chain or branched alkyl group having 1 to 15 carbon atoms, possibly comprising one or more unsaturations;
a substituted or unsubstituted aryl group having 6 to 10 carbon atoms;
a halogen atom selected from among chlorine, bromine, fluorine and iodine.

5. The process according to claim 1 wherein $R^3$ represents a heteroaryl having 5 to 10 members including at least one heteroatom selected from among a nitrogen atom or oxygen atom, unsubstituted or substituted by one or more substituents selected from among:
a straight-chain or branched group of formula —(O)$_n$alkyl having 1 to 15 carbon atoms, optionally substituted by one or more halogen atoms and n is 0 or 1;
a straight-chain or branched alkenyl group having 1 to 15 carbon atoms and comprising at least one double bond;
a halogen atom selected in particular from among chlorine, fluorine, bromine and iodine.

6. The process according to claim 1 wherein for the compounds of formula (I) and (III), $R^1$ is selected from among:
a hydrogen atom;
a straight-chain or branched alkyl group having 1 to 15 carbon atoms;
a straight-chain or branched alkenyl group having 1 to 15 carbon atoms and comprising at least one double bond;
an aryl group having 6 to 10 carbon atoms, unsubstituted or substituted by one or more substituents selected from among:
a halogen atom selected from among chlorine, bromine, fluorine or iodine;
a straight-chain or branched group of formula —(O)$_p$alkyl having 1 to 15 carbon atoms and p is 0 or 1;
a hydroxy group;
a straight-chain or branched alkenyl group having 1 to 15 carbon atoms and comprising at least one double bond; and
a straight-chain or branched trifluoroalkyl having 1 to 10 carbon atoms.

7. The process according to claim 1 wherein for the compounds of formula (I) and (III), $R^2$ is selected from among:
a straight-chain or branched alkyl group having 1 to 15 carbon atoms;
a straight-chain or branched alkenyl group having 1 to 15 carbon atoms and comprising at least one double bond;
an aryl group having 6 to 10 carbon atoms unsubstituted or substituted by one or more substituents selected from among:
a halogen atom selected from among chlorine, bromine, fluorine or iodine;
a hydroxy group;
a straight-chain or branched group of formula —(O)$_q$alkyl having 1 to 15 carbon atoms, and q is 0 or 1;
a straight-chain or branched alkenyl group having 1 to 15 carbon atoms and comprising at least one double bond; and
a straight-chain or branched trifluoroalkyl group having 1 to 10 carbon atoms.

8. The process according to claim 1 wherein X represents iodine.

9. The process according to claim 1 wherein the catalyst is selected from among metallic copper, copper(I) or copper (II) oxides, copper(I) or copper(II) hydroxides, inorganic or organic salts of copper(I) or copper(II) and complexes of copper(I) or copper(II) with ligands, or mixtures thereof.

10. The process according to claim 1 implemented in the presence of a solvent selected from among dioxane and tert-butanol.

11. The process according to claim 1 wherein the ligand is selected from among:
diketones of formula (i):

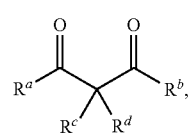

where:
$R^a$ and $R^b$, the same or different, represent a straight-chain or branched $C_1$ to $C_{10}$ alkyl chain, or $C_6$ to $C_{10}$ aryl radical;
$R^c$ and $R^d$ are a hydrogen atom; or
$R^a$ or $R^b$, together with their carrier group C(O) and with one of $R^c$ or $R^d$, forms a 6-membered carbocycle; and
diamines of formula (ii)

where:
$R^e$, $R^f$, $R^g$, $R^h$, the same or different, represent a hydrogen atom or $C_1$ to $C_{10}$ alkyl group;
r is an integer ranging from 1 to 10; or
aromatic polycyclic compounds having at least two heteroatoms, unsubstituted or substituted by one or more $C_1$ to $C_{10}$ alkyl groups, NO$_2$ group, aryl group having 6 to 10 carbon atoms.

12. The process according to claim 1 wherein the ligand is selected from among the compounds of formula:

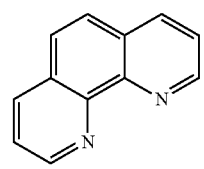

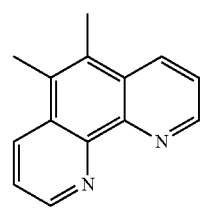

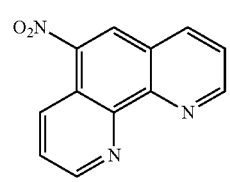

-continued (L4) 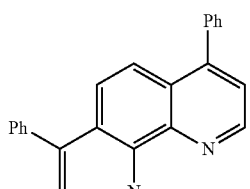

(L5) 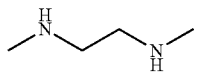

(L6) 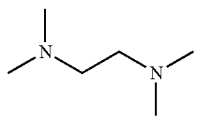

(L7) 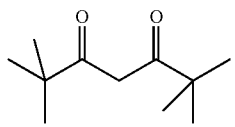

(L8) 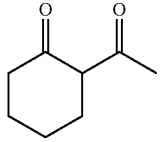

(L9) 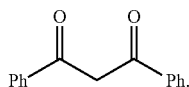

13. The process according to claim 1 wherein the base is selected from among:
alkaline or alkaline-earth alcoholates of formula $(M^1(OR)_s)$; and/or
alkaline or alkaline-earth phosphates of formula $(M^1_t(OH)_u(PO_4)_v)$; and/or
alkaline or alkaline-earth carbonates of formula $(M^1_w(CO_3)_y)$,
or mixtures thereof
wherein $M^1$ is Li, Na, K, Rb, Cs, Fr, Be, Mg, Ca, Sr, Ba or Ra; s is 1 or 2; R is selected from the group formed by the alkyl, benzyl and aryl groups; t is an integer ranging from 1 to 10; u is an integer ranging from 0 to 2; v is an integer ranging from 1 to 10; w is an integer ranging from 1 to 10; y is an integer ranging from 1 to 10.

14. The process according to claim 1 implemented at a temperature ranging from 50 to 200° C.

15. The process according to claim 1 wherein the molar quantity of catalyst is 0.001 to 100% relative to the number of moles of the formula (II) compound.

16. The process according to claim 1 wherein the ligand/catalyst molar ratio is 0.5 to 100.

17. The process according to claim 1 wherein the molar ratio of formula (II) compound/formula (III) compound is 0.5 to 10.

18. The process according to claim 1 wherein the molar quantity of base is 0.2 to 4 equivalents relative to the molar quantity of formula (II) compound.

19. A process for preparing a compound of formula (IV) comprising the implementing of the process according to claim 1:

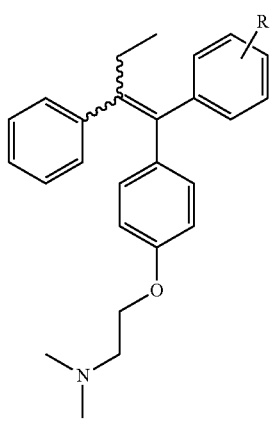

(IV)

wherein R is a hydrogen atom or hydroxyl group, comprising the following steps:
a) preparing a compound of formula (Ia) comprising the implementing of the process according to claim 1:

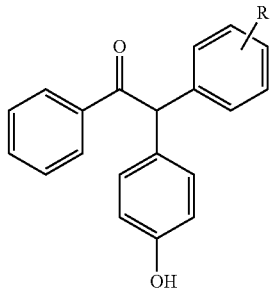

(Ia)

b) reacting the formula (Ia) compound with EtMgBr to obtain the compound of formula (V):

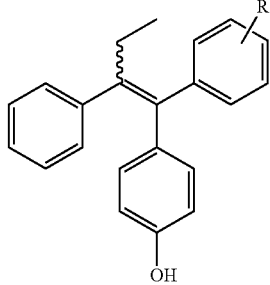

(V)

c) reacting the formula (V) compound with a compound of formula $Y-(CH_2)_2N(Me)_2$ where Y is a halogen atom, to obtain the compound of formula (IV).

20. A process for preparing a compound of formula (IV) comprising the following steps:
a) preparing a compound of formula (Ib) comprising the implementing of the process to create a C—C bond according to claim 1, in the presence of a compound of formula $Y-C_6H_4-O-(CH_2)_2N(Me)_2$ where Y is a halogen atom;

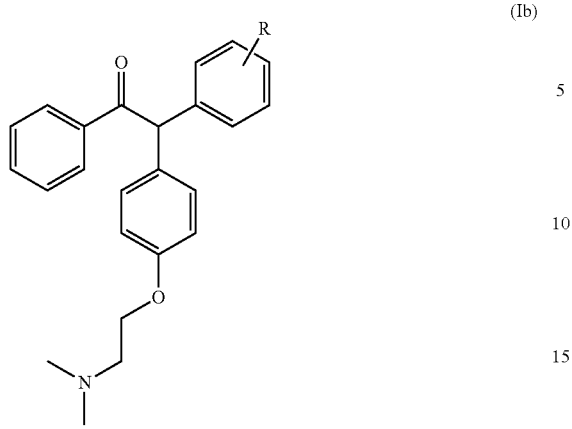
where R is a hydrogen atom or hydroxy group;
b) reacting the formula (Ib) compound with EtMgBr to obtain the compound of formula (IV).
* * * * *